(12) United States Patent
Koepsel et al.

(10) Patent No.: US 8,642,516 B2
(45) Date of Patent: Feb. 4, 2014

(54) CHEMICALLY-DEFINED ARRAYS FOR SCREENING CELL-SUBSTRATE INTERACTIONS

(75) Inventors: Justin T. Koepsel, Madison, WI (US); William L. Murphy, Waunakee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/465,120

(22) Filed: May 7, 2012

(65) Prior Publication Data

US 2013/0296177 A1 Nov. 7, 2013

(51) Int. Cl.
*C40B 60/14* (2006.01)
*C40B 60/00* (2006.01)
*C40B 40/00* (2006.01)

(52) U.S. Cl.
USPC .................................. 506/40; 506/33; 506/13

(58) Field of Classification Search
USPC ...................................................... 506/33, 40
See application file for complete search history.

(56) References Cited

U.S. PATENT DOCUMENTS

| | | | |
|---|---|---|---|
| 6,972,196 B1 * | 12/2005 | Mrksich et al. | 435/395 |
| 8,062,890 B2 | 11/2011 | Kiessling et al. | |
| 2006/0246583 A1 | 11/2006 | Murphy et al. | |
| 2010/0004137 A1 * | 1/2010 | Mrksich et al. | 506/12 |

OTHER PUBLICATIONS

Bietsch et al., Inkjet Deposition of Alkanethiolate Monolayers and DNA Oligonucleotides on Gold: Evaulation of Spot Uniformity by Wet Etching, Langmuir, 2004, 20, 5119-5122.*
Koepsel et al., Patterning Discrete Stem Cell Culture Environments via Localized Self-Assembled Monolayer Replacement, Langmuir, 2009, 25 (21), 12825-12834.*

* cited by examiner

*Primary Examiner* — Maria Leavitt
*Assistant Examiner* — Amy M Bunker
(74) *Attorney, Agent, or Firm* — Armstrong Teasdale LLP

(57) ABSTRACT

Patterned SAM arrays and methods of preparing patterned SAM arrays are disclosed. Advantageously, the methods used to prepare the patterned SAM arrays allow for controlling SAM spot-to-spot conditions such as ligand identity and ligand density, which allows for preparing a wide range of SAM spots in a single array format. Additionally, the patterned SAM arrays of the present disclosure support the culture of a range of cell types. The patterned SAM arrays offer the ability to rapidly screen substrate components for influencing cell attachment, spreading, proliferation, migration, and differentiation.

7 Claims, 33 Drawing Sheets

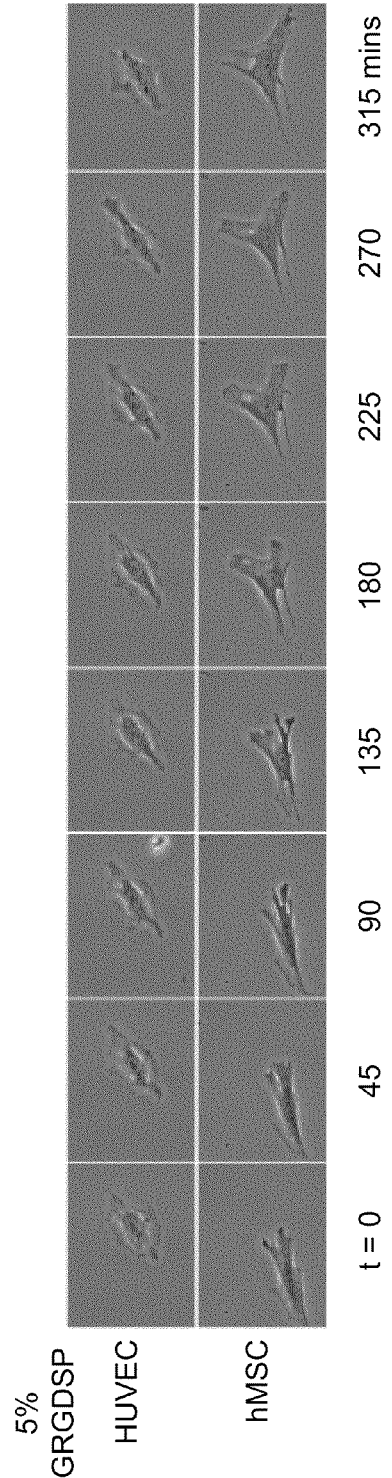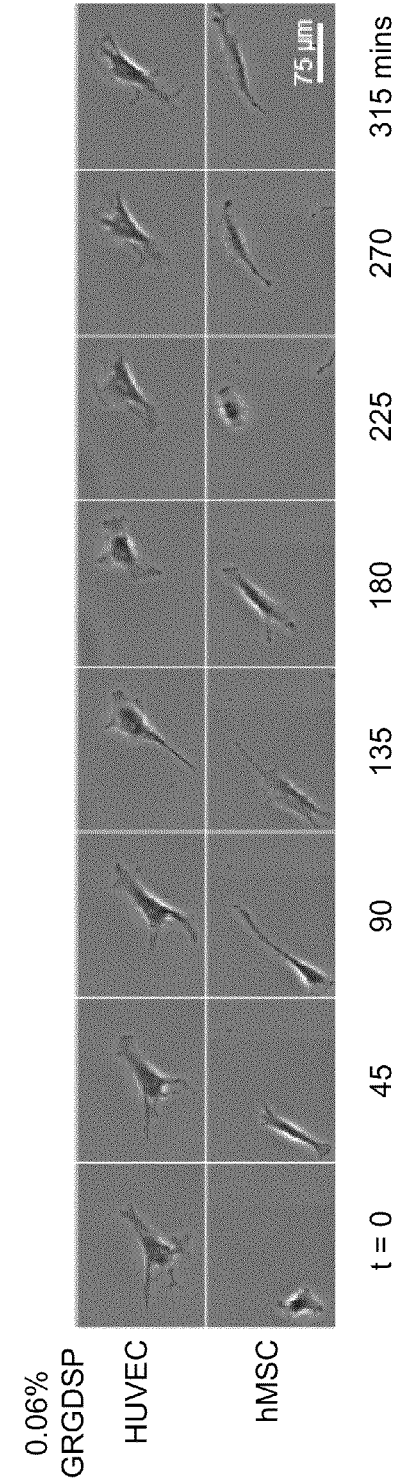

FIG. 17
X% HPG-BP 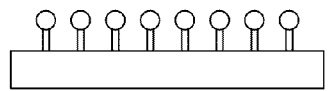
(100-X)% BR-BP
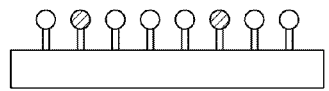
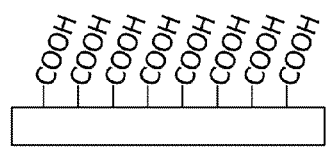  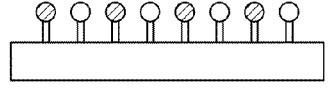
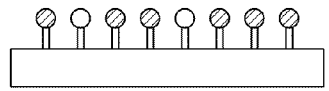
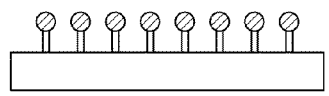

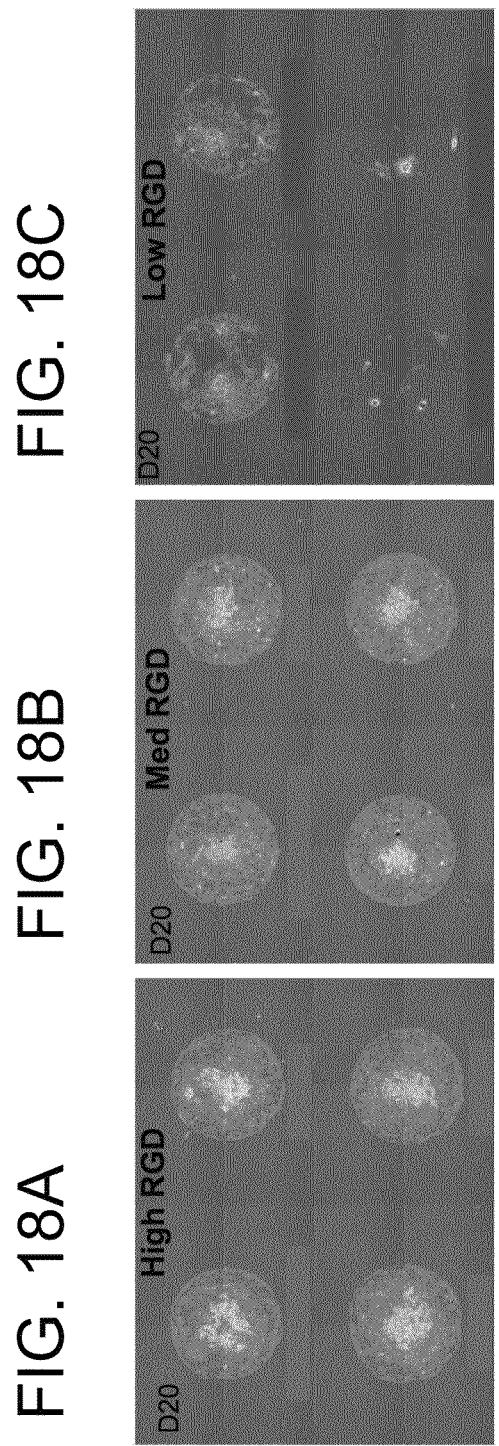

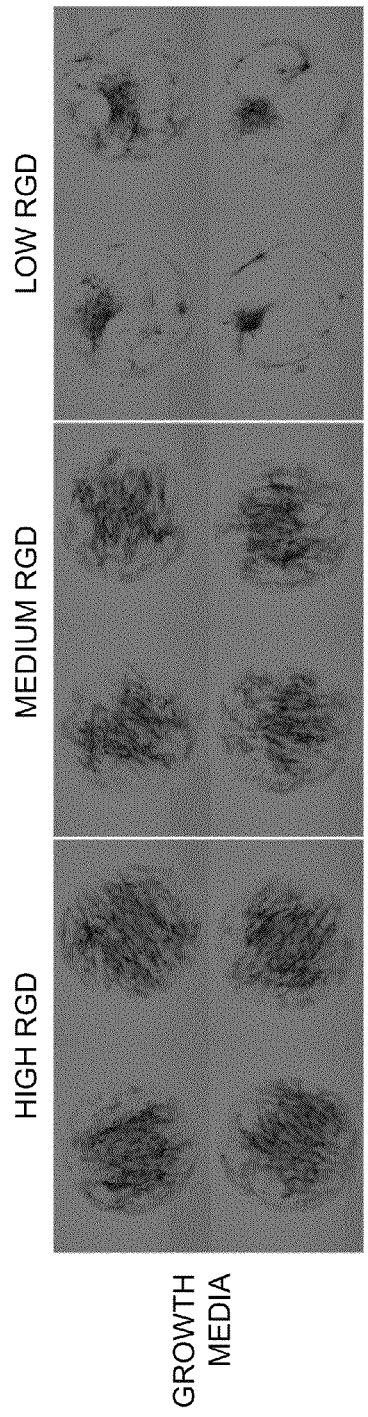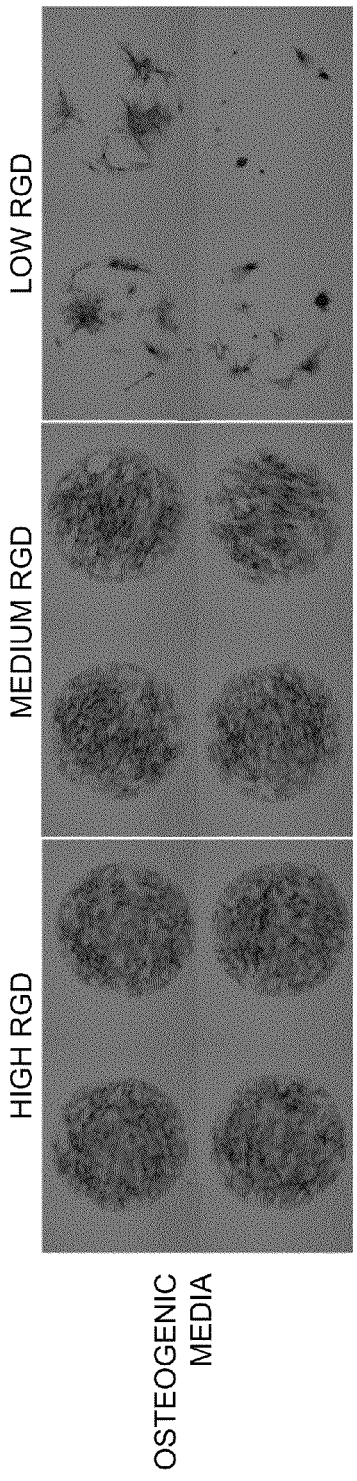

SEQUENCE LISTING

<160> NUMBER OF SEQ ID NOS: 19

<210> SEQ ID NO 1
<211> LENGTH: 18
<212> TYPE: PRT
<213> ORGANISM: Artificial Sequence
<220> FEATURE:
<223> OTHER INFORMATION: Synthetic

<400> SEQUENCE: 1

Gly Gly Gly Lys Leu Thr Trp Gln Glu Leu Tyr Gln Leu Lys Tyr Lys
1               5                   10                  15

Gly Ile

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Ser Asp Pro Gly Tyr Ile Gly Ser Arg
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Gly Arg Asn Ile Ala Glu Ile Ile Lys Asp Ile
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Asp Ile Thr Tyr Val Arg Leu Lys Phe
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Asp Ile Thr Val Thr Leu Asn Arg Leu
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Gly Arg Tyr Val Val Leu Pro Arg
1               5

<210> SEQ ID NO 7
<211> LENGTH: 13
<212> TYPE: PRT
<213> ORGANISM: Artificial Sequence
<220> FEATURE:
<223> OTHER INFORMATION: Synthetic

<400> SEQUENCE: 7

Gly Asn Arg Trp His Ser Ile Tyr Ile Thr Arg Phe Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Ser Ile Asp Gln Val Glu Pro Tyr Ser Ser Thr Ala Gln
1               5                   10

<210> SEQ ID NO 9
<211> LENGTH: 20
<212> TYPE: PRT
<213> ORGANISM: Artificial Sequence
<220> FEATURE:
<223> OTHER INFORMATION: Synthetic

<400> SEQUENCE: 9

Lys Ile Pro Lys Ala Ser Ser Val Pro Thr Glu Leu Ser Ala Ile Ser
1               5                   10                  15

Thr Leu Tyr Leu
            20

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Lys Lys Gln Arg Phe Arg His Arg Asn Arg Lys Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Gly Ala Ser Ile Lys Val Ala Val Ser Ala Asp Arg
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic

```
<400> SEQUENCE: 12

Gly Thr Thr Val Lys Tyr Ile Phe Arg
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Gly Ser Ile Lys Ile Arg Gly Thr Tyr Ser
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Gly Ser Ile Asn Asn Asn Arg
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

Lys Ile Pro Lys Ala Ser Ser Val Pro Thr Glu Leu
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Lys Arg Thr Gly Gln Tyr Lys Leu
1               5

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Lys Leu Thr Trp Gln Glu Leu Tyr Gln Leu Lys Tyr Lys Gly Ile
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Synthetic

<400> SEQUENCE: 18
```

```
Gly Arg Gly Asp Ser Pro
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Gly Arg Gly Glu Ser Pro
1               5
```

CHEMICALLY-DEFINED ARRAYS FOR SCREENING CELL-SUBSTRATE INTERACTIONS

STATEMENT OF GOVERNMENT SUPPORT

This invention was made with government support under EB005374 awarded by the National Institutes of Health. The government has certain rights in the invention.

INCORPORATION OF SEQUENCE LISTING

A paper copy of the Sequence Listing and a computer readable form of the Sequence Listing containing the file named "P120126 (28243-166)_ST25.txt", which is 4,089 bytes in size (as measured in MS-DOS), are provided herein and are herein incorporated by reference. This Sequence Listing consists of SEQ ID NOs: 1-19.

BACKGROUND OF THE DISCLOSURE

The present disclosure relates generally to chemically-defined arrays for screening cell-substrate interactions. More particularly, the present disclosure relates to self-assembled monolayer arrays with controlled ligand identity and variable ligand densities and to methods for preparing the self-assembled monolayer arrays. The present disclosure further relates to a method of screening a cell-surface interaction using the self-assembled monolayer arrays of the present disclosure.

The development of most tissue types involves a complex interplay of multiple signals leading to controlled precursor cell differentiation into mature, tissue-specific cell types. For example, mesenchymal stem cells (MSCs) may be differentiated in vitro into osteoblasts, chondrocytes, myoblasts, adipocytes, neurons, and endothelial cells by exposure to a variety of growth factors. Exposure to growth factors may be controlled by the media and the substrates upon which the cells are cultured. Substantial progress has been made in the development of defined media, but only more recently has the role of substrates and cell-substrate adhesion on cell growth been examined.

Based on studies to determine defined media, it has become apparent that the substrate is important for successful cellular growth and tissue generation. For example, it has been demonstrated that attachment to the substrate by human embryonic stem cells may contribute to the variability in whether the cells remain undifferentiated or undergo differentiation. Therefore, it is important to not only identify cell culture media for successful cell culture conditions, but to also identify defined substrates.

Screening well-defined surfaces in an array format allows rapid identification of specific molecules that promote cellular adhesion, cellular spreading, proliferation, migration and differentiation, as well as molecules that regulate cell behavior. Self-assembled monolayers ("SAMs") in array formats (i.e., SAM arrays) have been constructed that present ligands to cells plated onto the array. A SAM array is an organized layer of amphiphilic molecules in which one end of the molecule exhibits a specific, reversible affinity for a substrate and the other end of the molecule has a functional group. Because the molecule used to form the SAM array is polarized, the hydrophilic "head groups" assemble together on the substrate, while the hydrophobic tail groups assemble far from the substrate. Areas of close-packed molecules nucleate and grow until the surface of the substrate is covered in a single monolayer.

The use of alkanethiols to construct SAM arrays allow for the formation of reproducible SAM arrays and surfaces. SAM arrays may be used to identify specific ligands or epitopes that promote cellular attachment, spreading, proliferation, migration and differentiation. Additionally, SAM arrays may be patterned such that ligands will be presented to the cells in defined areas of the array.

While chemically-defined SAM array approaches have provided unique insights into several biological processes, SAM arrays have yet to become a commonly used tool for biology. One potential reason for their lack of use is that SAM array fabrication can be labor intensive. In typical experiments investigating SAM arrays presenting a range of different ligands or ligand densities, each condition and replicate requires an individual gold substrate. In most approaches, substrates are manually handled before and after each step of an experiment that can include gold substrate cleaning, SAM array formation, ligand conjugation, cell seeding, and analysis. Performing a SAM array-based experiment comparable to a standard 96-well plate may require close to 1000 handling steps before performing any type of analysis.

SAM array patterning approaches have been developed to spatially localize ligands to create spatially and chemically-defined cell culture substrates. Microcontact printing, for example, generates patterned SAM arrays by "inking" alkanethiolate molecules onto a flexible elastomeric stamp and stamping the alkanethiolates onto a gold surface, which transfers a pattern of ligands onto the gold substrate. The remaining areas of bare gold are then "backfilled" with a second alkanethiolate species to generate a bio-inert SAM surrounding the stamped hydrophobic alkanethiolate domains. The substrates are then bathed in a solution of ligands that spontaneously adsorb to the hydrophobic alkanethiolate regions to create patterned islands for cell attachment. Microfluidics approaches for SAM array patterning typically use elastomeric stamps with microscale features that form channels when passively adhered to a SAM. Localized ligand conjugation can then be achieved by flowing reaction solutions through the channels exposing them to reactive terminal moieties presented by the underlying SAM. Photochemistry in combination with micro-patterned photomasks can be used to create patterned SAM arrays by selectively protecting a reactive terminal moiety and then selectively deprotecting the terminal moiety to locally immobilize ligands on the SAM. SAM array patterning can also be accomplished by locally destroying/removing regions of a fully formed SAM, then reforming new SAMs in the destroyed regions.

While SAM arrays provide an excellent model substrate for investigating the effects of an immobilized ligand on cell behavior, preparing SAM array platforms using less labor intensive processes are needed to make SAM array use more widespread. Accordingly, there exists a need for alternative substrates with well-defined surfaces as well as methods for preparing these SAMs to identify surfaces that will support survival and growth of cells in culture.

SUMMARY OF THE DISCLOSURE

The present disclosure relates generally to self-assembled monolayer (SAM) arrays for screening cell-substrate interactions. More particularly, the present disclosure relates to patterned SAM arrays with controlled spot-to-spot ligand identity and density and to methods for preparing the SAM arrays. It has been found that the SAM arrays with controlled spot-to-spot ligand identity and density offer an improved screening method for cell-substrate interactions.

In one aspect, the present disclosure is directed to a method for preparing a self-assembled monolayer array. The method includes adhering a polymer stencil to a metal-coated substrate, wherein the polymer stencil comprises at least one well; forming an alkanethiolate self-assembled monolayer spot on the substrate, wherein the alkanethiolate self-assembled monolayer spot forms in the at least one well of the polymer stencil; removing the polymer stencil from the substrate; and backfilling a region on the substrate that surrounds the alkanethiolate self-assembled monolayer spot, wherein the backfilling forms a self-assembled monolayer surrounding the alkanethiolate self-assembled monolayer spot. In some embodiments, the method further includes immobilizing a ligand on the alkanethiolate self-assembled monolayer spot. In another embodiment, the method includes forming the alkanethiolate self-assembled monolayer spot using a ligand-alkanethiol conjugate. In other embodiments, the method further includes immobilizing a ligand on the self-assembled monolayer surrounding the alkanethiolate self-assembled monolayer spot. In yet further embodiments, ligands can be immobilized on the alkanethiolate self-assembled monolayer spot and the self-assembled monolayer surrounding the alkanethiolate self-assembled monolayer spot.

In another aspect, the present disclosure is directed to a self-assembled monolayer array comprising at least one alkanethiolate self-assembled monolayer spot; and a self-assembled monolayer surrounding the at least one alkanethiolate self-assembled monolayer spot, wherein the self-assembled monolayer surrounding the at least one self-assembled monolayer spot comprises a ligand.

In another aspect, the present disclosure is directed to a method of screening a cell-surface interaction. The method includes preparing a self-assembled monolayer array; contacting the cell to the self-assembled monolayer array; culturing the cell on the self-assembled monolayer array; and analyzing the cell. The self-assembled monolayer array is prepared by adhering a polymer stencil to a metal-coated substrate, wherein the polymer stencil comprises at least one well; forming at least one alkanethiolate self-assembled monolayer spot on the substrate, wherein the alkanethiolate self-assembled monolayer spot is formed in the at least one well of the polymer stencil; removing the polymer stencil from the metal-coated substrate; and backfilling a region on the metal-coated substrate that surrounds the at least one alkanethiolate self-assembled monolayer spot, wherein the backfilling forms a self-assembled monolayer surrounding the at least one alkanethiolate self-assembled monolayer spot. The self-assembled monolayer spot and/or the self-assembled monolayer that surrounds the at least one alkanethiolate self-assembled monolayer spot further includes an immobilized ligand that is known or suspected of binding with the cell.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 13A and 13B are phase contrast images showing cell migration of HUVEC and hMSC on SAM array spots presenting (A) 5% and (B) 0.06% ligand taken every 15 minutes over 12-18 hours as discussed in Example 4.

FIG. 17 is a schematic illustrating mixed HPG-BP and BMP peptide immobilized on SAM array spots as discussed in Example 5.

FIGS. 18A-18C are phase contrast images of hMSCs cultured for 20 days on SAM array spots presenting varied ligand densities with combinations of BR-BP and HPG-BP peptides as discussed in Example 6.

FIGS. 20A-20F are phase contrast images of hMSCs cultured for 7 days on SAM array spots presenting variable ligand densities with combinations of BR-BP and HPG-BP peptides and cultured in growth media or osteogenic media as discussed in Example 7.

Figure 1:
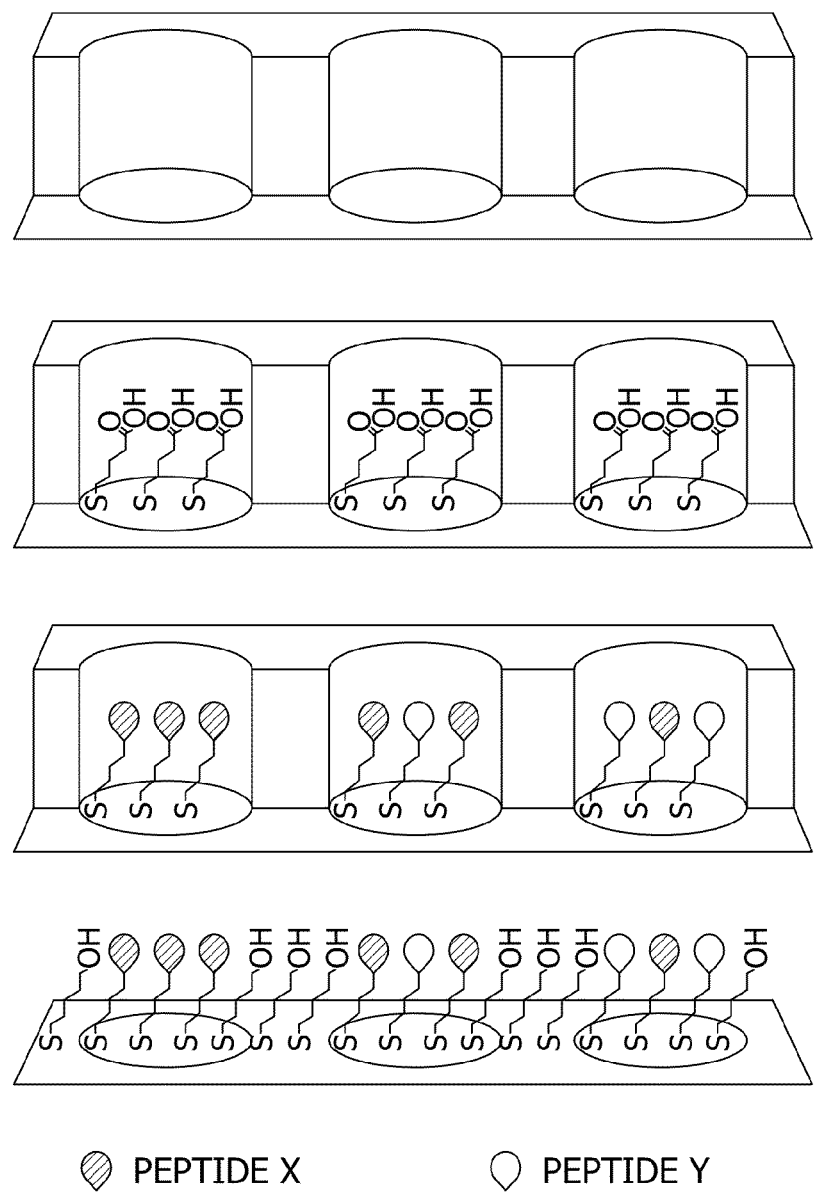
FIG. 1 is a schematic illustrating the steps for preparing a self-assembled monolayer array using the methods of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, methods for preparing chemically-defined arrays for screening cell-substrate interactions have been discovered. More particularly, the present disclosure relates to SAM arrays with controlled spot-to-spot ligand identity and density and to methods for preparing the SAM arrays. It has been found that the SAM arrays with controlled spot-to-spot ligand identity and density offer an improved screening method for cell-substrate interactions.

Methods of Preparing SAM Arrays

In one aspect, the present disclosure is directed to a method for preparing a SAM array, the array having controlled spot-to-spot ligand identity and density. The method generally includes: adhering a polymer stencil to a metal-coated substrate; introducing an alkanethiol solution into at least one well of the polymer stencil to form at least one alkanethiolate self-assembled monolayer spot (i.e., alkanethiolate SAM spot); removing the polymer stencil; and backfilling a region surrounding the alkanethiolate SAM spot, thereby forming a SAM surrounding the alkanethiolate SAM spot. In use, the S—H head group of the alkanethiol attaches to the metal-coated substrate, while the opposing tail group is available to bind with one or more ligands. In one embodiment, the ligand may be bound prior to the formation of the alkanethiolate SAM spot by introducing the ligand into the alkanethiol solution. In an alternative embodiment, the ligand is bound to the alkanethiolate SAM spot after formation of the alkanethiolate SAM spot in the well of the polymer stencil. As used herein, the term "alkanethiol" refers to any molecule that has an alkanethiol moiety. Suitable alkanethiols may be, for example, alkanethiols with different "non-fouling" moieties such as, for example, oligo(ethylene glycol), fluorocarbons, glucamine, as well as ligand-alkanethiol conjugates.

The method initially includes adhering a polymer stencil to a metal-coated substrate. Suitable substrates for use in the methods of the present disclosure are those known to one skilled in the art such as, for example, glass microscope slides, glass microscope coverslips, and the like.

The substrate may be coated with a metal using methods known to those skilled in the art such as, for example, evaporation, vapor deposition, electrodeposition, and electroless deposition. Particularly suitable metals may be, for example, gold, titanium, copper, stainless steel, silver, platinum, ruthenium, rhodium, palladium, osmium, iridium and combinations thereof. Using the metal substrates above has an advantage as the metal and alkanethiols have a strong affinity, and thus, form stable bonds.

In one particular embodiment, a metal-coated substrate is a gold-coated substrate that is commercially available from Platypus Technologies, LLC (Madison, Wis.).

The method further includes adhering a polymer stencil to the metal-coated substrate. See, FIG. 1. The polymer stencil is typically a thin polymer film having at least one hole, which when adhered to the substrate forms at least one well. When adhered to the substrate, the polymer stencil blocks or "masks" the surface of the metal-coated substrate such that only a portion of the substrate is exposed where a hole in the stencil exists. In this manner, the polymer stencil blocks the alkanethiol solution from areas outside the well and contains the alkanethiol solution within the well-portion of the polymer stencil. The polymer stencil may be formed using any suitable polymer known to those skilled in the art. A particularly suitable polymer stencil may be, for example, polydimethylsiloxane (PDMS).

An alkanethiol solution is then deposited into each well of the polymer stencil, which forms a self-assembled monolayer (alkanethiolate SAM) spot on the substrate in each well of the polymer stencil. See, FIG. 1.

As known by those skilled in the art, alkanethiols are molecules with a S—H head group, an alkyl chain as a backbone, and a tail group that may be functionalized to have affinity for ligands such as, for example, peptides, proteins, nucleic acids, polysaccharides, lipids, cells and other molecules. In the case of alkanethiols, the attachment moiety is the thiol group, which has a strong affinity for metal-coated substrates and assemble together on the substrate. The alkanethiol molecules continue to assemble until the surface of the substrate is covered to form an alkanethiolate monolayer.

Particularly suitable alkanethiols are illustrated below:

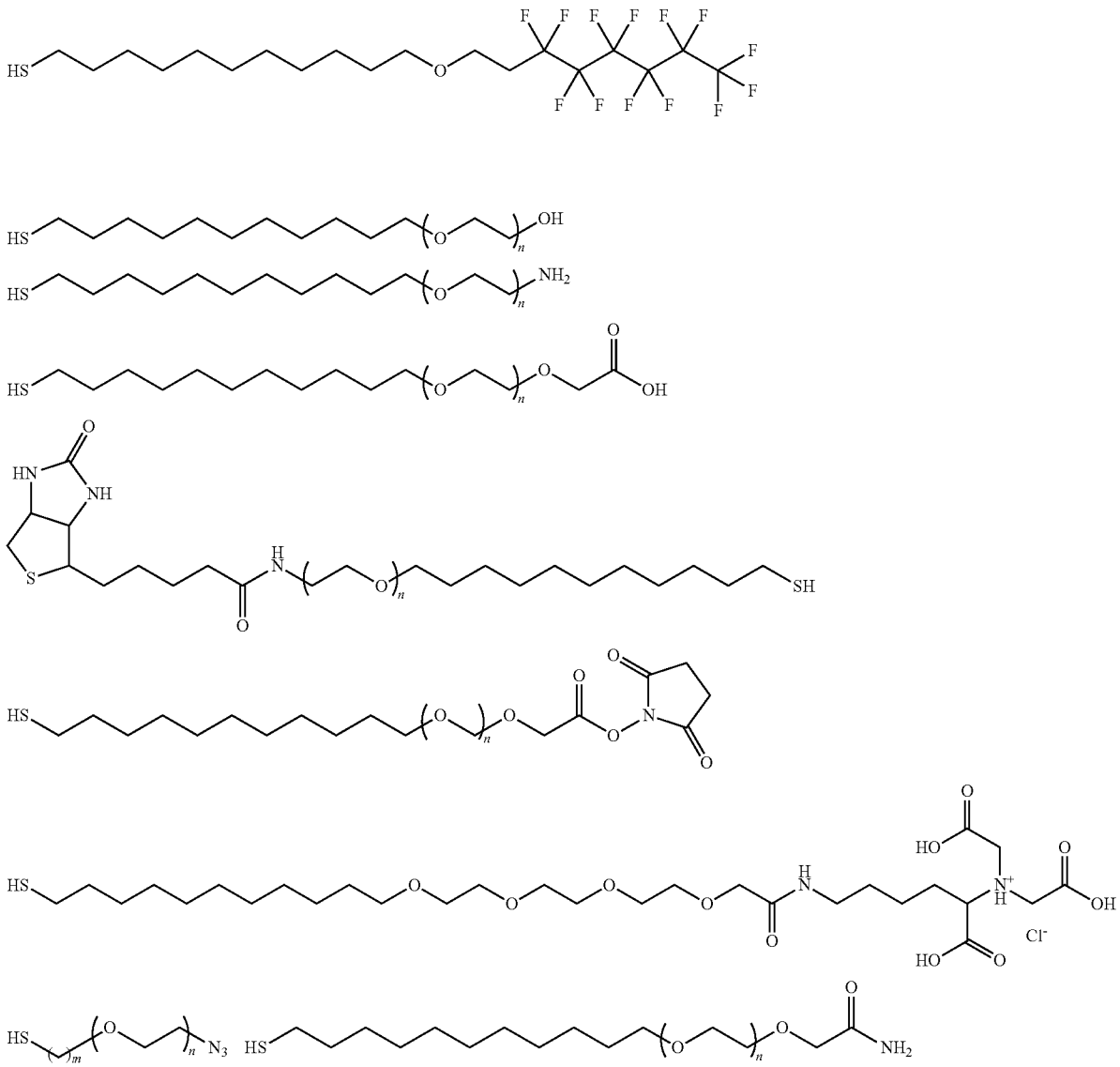

-continued

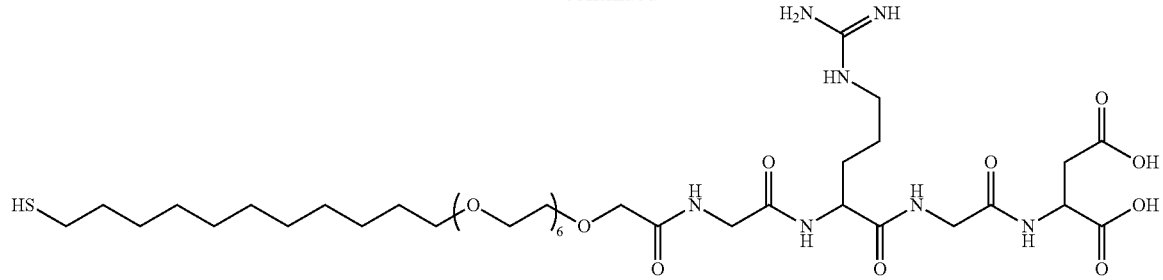

It should be appreciated that the pattern of alkanethiolate SAM spots may easily be controlled and adjusted by adjusting the stencil used, and the pattern may typically depend on the desired end use of the SAM array. Without being limiting, for example, patterns of alkanethiolate SAM spots may be created on the metal-coated substrate in rows, spirals, circles, squares, rectangles, combinations thereof, and the like.

In one embodiment, following alkanethiolate SAM spot formation in the individual wells of the polymer stencil, the method may further include immobilizing at least one ligand on the alkanethiolate SAM spot formed in the wells of the polymer stencil. See, FIG. 1. Immobilization chemistries for immobilizing different types of ligands are known to those in the art. Suitable immobilization chemistries may be, for example, carbodiimide reactions between primary amine and carboxylate groups, click reactions between moieties such as, for example, azide and alkyne groups and thiol and alkene groups, Diels-Alder reactions between hydroquinone and dienes, reactions between maleimide and sulfhydrals, Schiff base formation between aldehydes and primary amines, and combinations thereof.

In an alternative embodiment, alkanethiol solutions having an immobilized ligand already attached to the alkanethiol (i.e., pre-conjugated) may be added to the well of the polymer stencil to form an alkanethiolate SAM spot including at least one ligand. Suitable methods for using alkanethiols with pre-conjugated ligands may be, for example, cell adhesion ligands such as, for example, Arg-Gly-Asp (RGD), biotin-streptavidin interactions, poly-histidine interactions with nitrolotriacetic acid-bound $Ni^{2+}$, and combinations thereof.

Advantageously, the identity and the density of the immobilized ligand in the alkanethiol SAM spot may be controlled. In one aspect, the density of the immobilized ligand may be controlled by controlling the concentration of the alkanethiol in the alkanethiol solution prior to alkanethiolate SAM spot formation. In another aspect, the density of the immobilized ligand may be controlled by controlling the concentration of the ligand in the alkanethiol solution used for immobilization of the ligand in the alkanethiolate SAM spot. In yet another aspect, the density of the immobilized ligand may be controlled by controlling the amount of alkanethiol solution (including the immobilized ligand) to be deposited within a well of the polymer stencil. In yet another aspect, the density of the immobilized ligand may be controlled by mixing a ligand with a second species of ligand to be conjugated to the surface.

Suitable ligands may be, for example, peptides, proteins, nucleic acids, polysaccharides, lipids, and other molecules, and combinations thereof. Particularly suitable peptides and proteins may be, for example, RGD, GGGKLTWQE-LYQLKYKGI (SEQ ID NO:1), SDPGYIGSR (SEQ ID NO:2), GRNIAEIIKDI (SEQ ID NO:3), DITYVRLKF (SEQ ID NO:4), DITVTLNRL (SEQ ID NO:5), GRYVVLPR (SEQ ID NO:6), GNRWHSIYITRFG (SEQ ID NO:7), SIDQVEPYSSTAQ (SEQ ID NO:8), KIPKASSVPTEL-SAISTLYL (SEQ ID NO:9), KKQRFRHRNRKG (SEQ ID NO:10), GASIKVAVSADR (SEQ ID NO:11), GTTVKYIFR (SEQ ID NO:12), GSIKIRGTYS (SEQ ID NO:13) and GSINNNR (SEQ ID NO:14), bone morphogenetic protein-2 (BMP-2) receptor binding peptide (KIPKASSVPTEL; SEQ ID NO:15), heparin proteoglycan-binding peptide (HPG-BP) (KRTGQYKL; SEQ ID NO:16), vascular endothelial growth factor receptor binding peptide (referred to herein as "VR-BP"; KLTWQELYQLKYKGI, SEQ ID NO: 17), GRGDSP (SEQ ID NO:18) and combinations thereof. In another aspect, ligands may be ligands suspected of binding or interacting with a cell to affect cell attachment, spreading, migration, proliferation, and differentiation, which are immobilized to the alkanethiolate SAM spot and screened for cell attachment, spreading, migration, proliferation, and differentiation function. Additionally, ligands of unknown function may be immobilized in combination with a cell attachment ligand to screen for changes in cell attachment, spreading, migration, proliferation, and differentiation.

Following the formation of the alkanethiolate SAM spots in the individual wells of the polymer stencil, the polymer stencil is removed from the substrate. Removal of the polymer stencil results in individual alkanethiolate SAM spots separated by bare regions of the metal-coated substrate lacking alkanethiolate molecules or monolayers. See, FIG. 1. The alkanethiolate self-assembled monolayer spots may have any desired diameter. Particularly suitable diameters of alkanethiolate self-assembled monolayer spots may be about 10 μm and larger.

The method of the present disclosure then includes backfilling the bare region of the metal-coated substrate surrounding the alkanethiolate SAM spots. To backfill the bare region of the metal-coated substrate, an alkanethiol solution is deposited on the substrate after the removal of the polymer stencil similarly as described above for deposition of the solution in the well. Suitable alkanethiols may be those described herein. Particularly suitable alkanethiols may be, for example, oligo(ethylene glycol) terminated alkanethiols. The backfilling forms a SAM that surrounds the alkanethiolate SAM spots previously formed in the wells of the polymer stencil.

Upon completion of the backfilling step, the resultant SAM array includes individual alkanethiolate SAM spots that may be of variable ligand identity and/or ligand density within the SAM (i.e., the backfilled region of the array). See, FIG. 1. In addition to separating individual alkanethiolate SAM spots from one another, the SAM array may also generally resist cell attachment.

SAM arrays may be analyzed to determine ligand incorporation on the alkanethiolate SAM spots. Suitable methods for analyzing SAM arrays for incorporation of ligands may be by fluorescence imagining. For example, epsilon primary amine groups present in lysine residues of the ligand maybe labeled with a fluorescent molecule. Following immobilization of the labeled ligand onto alkanethiolate SAM spots, the SAM arrays containing the fluorescently-labeled ligand may be scanned for fluorescence using any fluorescence detecting imagining equipment. One suitable fluorescence detecting imagining equipment for use in analyzing the SAM arrays formed using the above methods include GE Healthcare Typhoon Trio Variable Mode Imager.

In another aspect, the present disclosure is directed to a SAM array including a controlled ligand identity and/or variable ligand density prepared according to the method described herein.

The SAM array generally includes at least one alkanethiolate SAM spot and a SAM (backfilled region described above) that surrounds and/or separates individual alkanethiolate SAM spots. In one aspect, for example, the SAM array includes a first alkanethiolate SAM spot having a first ligand density and at least a second alkanethiolate SAM spot having a second ligand density. A SAM surrounds and separates the first and second alkanethiolate SAM spots. While described herein as having first and second alkanethiolate SAM spots, one skilled in the art would readily understand that the SAM array may include more than two alkanethiolate SAM spots. For example, the number of spots may range from two to 120 or more spots. The ligand density of the first alkanethiolate SAM spot may be different from the ligand density of the second alkanethiolate SAM spot. The SAM array also includes a SAM surrounding the first alkanethiolate SAM spot and the second alkanethiolate SAM spot.

The ligand density of the alkanethiolate SAM spot may range up to 7.7 pmol/mm$^2$ for a planar surface. For example, the ligand density may be from 0 pmol/mm$^2$ to about 7.7 pmol/mm$^2$. Suitable ligands are described herein.

The SAM backfilled region may further function to generally resist cell attachment as they lack any functional moiety or group to which cells may bind. In another aspect, the SAM of the backfilled region may be modified to attach one or more ligands that are different than the ligand incorporated into the alkanethiolate SAM spot(s). In this manner, the backfilled SAM would be considered to have a different functionality than the alkanethiolate SAM spot(s).

The SAM array may further include alkanethiolate SAM spots having different ligand identities. Suitable ligands are those described herein. The ligand is immobilized to the alkanethiolate SAM spots and/or SAM (backfilled region) as described herein.

Methods of Screening a Cell-Surface Interaction Using the SAM Arrays

In another aspect, the present disclosure is directed to a method of screening a cell-surface interaction. The method includes preparing a SAM array as described herein. A ligand to be screened is immobilized to a SAM spot as described herein. Additionally, or alternatively, a ligand to be screened may be immobilized to the SAM of the backfilled region surrounding the SAM spot as described above. The ligand to be screened using the SAM array of the present disclosure may be a ligand that is known or suspected of binding or interacting with a cell.

The method further includes contacting a cell with the SAM spots. The cells are then cultured for a desired time. After the desired time, cells are analyzed by microscopy such as, for example, immunofluorescence microscopy, phase contrast microscopy, light microscopy and combinations thereof. Cells may be analyzed for cell attachment, cell spreading, cell morphology, cell proliferation, cell migration, cell differentiation, protein expression, and combinations thereof.

Suitable cells may be any cell known by those skilled in the art. Particularly suitable cells may be, for example, mesenchymal stem cells (MSCs), umbilical vein endothelial cells (UVECs), NIH 3T3 fibroblasts, dermal fibroblasts(DFs), fibrosarcoma cells (HT-1080s), and embryonic stem cells (ESCs).

The method may further include contacting the cell with a soluble molecule by including the soluble molecule in the culture medium in which the cells on the alkanethiolate SAM spots are cultured. Particularly suitable soluble molecules may be growth factors and proteoglycans. Suitable growth factors may be, for example, proteins from the transforming growth factor beta superfamily, fibroblast growth factor family of growth factors, platelet derived growth factor family of growth factors and combinations thereof. Particularly suitable growth factors may be, for example, vascular endothelial growth factor, bone morphogenetic proteins, fibroblast growth factor, insulin-like growth factor and combinations thereof. Suitable proteoglycans may be, for example, proteoglycans with heparin, heparan, or chondroitin glycosaminoglycan side chains.

The methods and SAM arrays of the present disclosure allow for exceptional control over the density of the ligand on the SAM spot as well as exceptional control over the identity of the ligand on the SAM spot. This allows for screening for specific parameters of substrates for the culture of cells, which may alter and influence the outcome of the cellular response to the substrate and culture environment. The SAM arrays of the present disclosure further allow for screening combinations of ligands. Thus, the SAM arrays of the present disclosure present a tool to perform high-throughput multivariable biological screens on a single surface for identifying specific parameters of substrates that may alter and influence the outcome of the cellular response to the substrate and culture environment.

The disclosure will be more fully understood upon consideration of the following non-limiting Examples.

EXAMPLES

Example 1

In this Example, a SAM array having a controlled ligand composition was prepared to screen for changes in human mesenchymal stem cell behavior.

Carboxylic acid-capped hexa(ethylene glycol) undecanethiole (HS—$C_{11}$—(O—$CH_2$—$CH_2$)$_6$—O—$CH_2$—COOH) (referred to herein as "HS—$C_{11}$-$EG_6$-COOH"), was purchased from Prochimia (Sopot, Poland). 11-tr(ethylene glycol)-undecane-1-thiol (HS—$C_{11}$—(O—$CH_2$—$CH_2$)$_3$—OH (referred to herein as "HS—$C_{11}$-$EG_3$-OH") was synthesized as described in (Prime and Whitesides, J. Am. Chem. Soc. 115(23)):10714-10721 (1993)). Fmoc-protected amino acids and Rink amid MBHA peptide synthesis resin were purchased from NovaBiochem (San Diego, Calif.). Hydroxybenzotriazol (HOBt) was purchased from Advanced Chemtech (Louisville, Ky.). Diisopropylcarbodiimide (DIC) was purchased from Anaspec (San Jose, Calif.). N-hydroxysuccinimide (NHS), n-(3-dimethylaminopropyl)-N'-ethylcarbodiimide hydrochloride (EDC), sodium dodecyl sulfate (SDS), trifluoroacetic acid (TFA), diethyl ether, and deionized ultrafiltered water (DIUF $H_2O$) were purchased from Fisher Scientific (Fairlawn, N.J.). Triisopropylsilane (TIPS), piperidine, dimethylformamide (DMF), acetone, hexanes, and acetonitrile were purchased from Sigma-Aldrich (St. Louis, Mo.). Absolute ethanol (EtOH) was purchased from AAPER Alcohol and Chemical Co. (Shelbyville, Ky.). All purchased items were of analytical grade and used as received. Thin films of 100 Å Au <111>, 20 Å Ti on 1"×3"× 0.040" glass were purchased from Platypus Technologies, LLC (Madison, Wis.).

Standard solid phase Fmoc-peptide synthesis (Fmoc SPPS) was performed to synthesize peptides using a 316c automated peptide synthesizer (C S Bio, Menlo Park, Calif.). Rink amide MBHA resin was used as the solid phase, and HOBt and DIC were used for amino acid activation and coupling. After coupling the final amino acid, a 4-hour incubation in TFA, TIPS, and DIUF (95:2.5:2.5) released the peptide from resin and removed protecting groups. Released peptide was extracted from the TFA/TIPS/DIUF cocktail via precipitation in cold diethyl ether. Lyophilized peptides were analyzed using matrix-assisted laser desorption/ionization-time-of-flight (MALDI-TOF) mass spectrometry with a Bruker Reflex II (Billerica, Mass.). The purity of synthesized peptides was verified to be greater than 90% via HPLC using a C18 analytical column (Shimadzu, Kyoto, Japan) with a gradient of 0-70% $H_2O$+0.1% TFA/acetonitrile and a flow rate of 0.9 mL/minute. GWGGRGDSP and GWGGRGESP adhesion and mutant peptides were synthesized with tryptophan-bearing spacers to aid in determination of peptide concentration via UVN is. Peptide stocks were prepared at 300 µM in PBS as pH 7.4 as determined by absorbance at 280 nm using extinction coefficients outlined by Gill and von Hippel (Analytical Biochemistry 182(2):319-326 (1989)). Fluorescently-labeled GGRGDSPK was synthesized as previously described (Koepsel and Murphy, Langmuir 25(21): 12825-34 (2009)) and peptide concentration was determined by absorbance of the 5(6)-carboxyfluorescein group at 492 nm using an extinction coefficient of 81,000 $cm^{-1}M^{-1}$.

Polymer stencils containing arrays of wells were created using soft lithography. Master molds containing arrays of 1100 µm diameter posts were fabricated from SU-8 (Microchem, Newton, Mass.) spin-coated silicon wafers using conventional photolithography techniques. Polydimethylsiloxane (PDMS) (Sylgard 184, Dow Corning, Midland, Mich.) was prepared by mixing a 10:1 ratio of base/curing agent (w/w) followed by degassing for ~30 minutes. The degassed mixture was cast over the mold and cured for 4 hours at 85° C. Following curing, PDMS stencils were removed from molds and cleaned in hexanes using overnight Soxhlet extraction. After cleaning, stencils were placed in vacuo to remove residual solvent from the Soxhlet extraction process.

Gold slides were placed into a 150 mm glass Petri dish, covered with EtOH and sonicated for ~1 min. using an ultrasonic bath (Bransonic 1510, Branson, Danbury, Conn.). Sonicated gold chips were then rinsed with EtOH and blown dry with $N_2$. As illustrated in FIG. 1, SAM arrays were fabricated as follows: An elastomeric (polymer) stencil containing arrays of 1.1 mm holes was placed on a bare gold surface to form an array of wells on the gold substrate. Wells were then filled with 1 mM ethanolic alkanethiolate solution and incubated for 10 minutes in a chamber containing a laboratory wipe soaked in ethanol to prevent evaporation during local SAM formation. Alkanethiolate solutions were then aspirated and wells were rinsed with DIUF $H_2O$. Carboxylate groups were then converted to active ester groups by adding a solution of 100 mM NHS and 250 mM EDC in DIUF $H_2O$ pH 5.5 to wells and incubated for 10 minutes. After an additional rinse with DIUF $H_2O$, 300 µM solutions of peptide in PBS and pH 7.4 were added to each well and incubated for 1 hour in a humidity controlled chamber to covalently couple peptides to each array spot. After a final rinse in DIUF $H_2O$, regions surrounding array spots were backfilled with HS—$C_{11}$-$EG_3$-OH. This was accomplished by submerging the gold substrate and attached elastomeric stencil in an aqueous 0.1 mM HS—$C_{11}$-$EG_3$-OH solution (pH 2.0), removing the stencil, and incubating for 10 minutes. Following backfilling, the array was rinsed with 0.1 wt % SDS in DIUF $H_2O$, DIUF $H_2O$, and EtOH and then dried under a stream of $N_2$. Arrays were stored in sterile DIUF $H_2O$ at 4° C. and used within 24 hours.

In this SAM array approach, each spot was designed to contain the same total molar density ($mol/cm^2$) of peptide from spot to spot. Therefore, control over GRGDSP (SEQ ID NO:18) density was achieved by mixing GRGDSP (SEQ ID NO:18) with the mutant GRGESP (SEQ ID NO:19) peptide. In a typical SAM array, SAMs were locally formed within spots using a 1 mM alkanethiolate mixture of 95% HS—$C_{11}$-$EG_3$-OH and 5% HS—$C_{11}$-$EG_6$-COOH to create surfaces with a total of 5% carboxylate groups for peptide conjugation. Here, "X %" refers to the mole percent of alkanethiolate present during SAM formation and subsequently the approximate amount of an alkanethiolate present on the surface after SAM formation. Next, to create a spot presenting 5% GRGDSP (SEQ ID NO:18), a 300 µM peptide solution was used during peptide conjugation. Likewise, to create a spot with 1.6% GRGDSP (SEQ ID NO:18), a 300 µM peptide solution with 100 µM GRGDSP (SEQ ID NO:18) and 200 µM GRGESP (SEQ ID NO:19) was used during the peptide conjugation. In this manner, the amount of GRGDSP (SEQ ID NO:18) peptide could be varied between spots while holding total peptide content constant.

Passage 2 human umbilical vein endothelial cells (HUVEC) were expanded at low density (less than 70% confluence) on tissue culture polystyrene to no more than 14 population doublings. During HUVEC expansion and experiments on SAM arrays, HUVECs were cultured in medium 199 (Mediatech, Manassas, Va.) containing 1% penicillin/streptomycin (Hyclone, Logan, Utah) and supplemented with Clonetics EGM-2 BulletKit (Lonza Walkersville, Inc., Walkersville, Md.) containing hydrocortisone, hFGF-B, VEGF, $R^3$-IGF-1, ascorbic acid, heparin, fetal bovine serum, hEGF, GA-1000 growth supplements. Bone marrow-derived human mesenchymal stem cells (hMSC) (Lonza) were expanded at low density on tissue culture polystyrene plates to maintain multipotency as described by Sotiropoulou et al. (Stem Cells 24(2):462-471 (2006)) and used by passage 7. During hMSC expansion and experiments on SAM arrays, hMSCs were cultured in minimum essential medium, alpha (Mediatech, Manassas, Va.) containing 10% MSC qualified fetal bovine serum (Invitrogen, Carlsbad, Calif.) and 1% penicillin/streptomycin.

For cell assays on SAM arrays, HUVECs or hMSCs were removed from plastic culture plates using a 0.05% trypsin solution, resuspended in media, and seeded onto SAM arrays in sterile polystyrene Petri dishes. After allowing cells to attach for ~1 hour in a humidified incubator at 37° C. and 5% $CO_2$, arrays were dipped in warm media to remove loosely attached cells and then transferred to a rectangular multidish (Thermo Scientific/Nunc, Rochester, N.Y.) with warm media and imaged ~4 hours later serving as "0 hr." For the initial time point and subsequent time-lapse imaging, arrays were placed on an incubated stage and each array spot was imaged every 15 minutes for 72 hours. Furthermore, it is important to point out that all cell experiments for comparison between HUVECs and hMSCs were run simultaneously.

For immunocytochemistry, at 24 and 72 hour time points during the time-lapse experiment, staining for the actin cytoskeleton and focal adhesion markers was performed as directed by the manufacturer (Catalog No. FAK100, Millipore, Billerica, Mass.). Briefly, cells on arrays were fixed using 4% formaldehyde in PBS for 15 minutes. Following fixing, arrays were washed and then permeabilized using 0.1% Triton X-100 (MP Biomedicals, Aurora, Ohio) in PBS for 5 minutes. After an additional wash and a blocking step using 1% (w/v) bovine serum albumin (Fisher Scientific, Fairlawn, N.J.) arrays were exposed to a PBS solution containing an anti-vinculin primary antibody for 1 hr at room temperature. Arrays were then exposed to a PBS solution containing a FITC-conjugated secondary antibody and TRITC-conjugated phalloidin for 60 minutes at room temperature. After a final rinse, arrays were mounted with a cover slip using Prolong Gold Antifade Reagent with DAPI (Invitrogen, Eugene, Oreg.) as indicated by the manufacturer.

For array imaging, a GE Healthcare Typhoon Trio Variable Mode Imager was used to scan SAM arrays containing fluorescently-labeled peptide and fluorescent intensity was quantified using Image J (ImageJ, Freeware, NIH, Bethesda, Md.) imaging software. Cells in culture on SAM arrays were imaged using a Nikon Eclipse Ti inverted microscope equipped with the Perfect Focus System; filters for FITC, TexasRed, and DAPI; and a TIZ Tokai Hit incubated stage that was humidified and maintained at 37° C. and 5% $CO_2$. For phase contrast imaging, a 10× PhL objective was used to capture 4 images of each spot, which were automatically stitched together using the Nikon NIS Elements software. Immunofluorescence images of each array spot were acquired at 30× and stitched together from 20 images. For immunofluorescence imaging, exposure times for each channel were kept constant from array to array.

Relative cell attachment at 0 hrs was quantified by counting the number of attached cells per spot and normalizing cell numbers to maximal attachment conditions. Normalized cell number was calculated by dividing the number of cells per spot at 72 hours ($C_{72}$) to the cell number observed on the same spot at 0 hrs ($C_0$). Relative proliferation was determined by dividing normalized cell numbers at 72 hours by the maximum average normalized cell number observed across GRGDSP density conditions. Similarly, relative spreading was determined by dividing projected cell areas to the maximum average projected cell area observed across GRGDSP density conditions. Analysis of projected cell area was achieved using Nikon NIS Elements Software (Melville, N.Y.). Briefly, stacked images of array spots were thresholded and then automated measurements of area and counts were tabulated. For each spot, average cell projected area was calculated by dividing the thresholded actin staining (red channel) by the total number of nuclei in the same spot. For cell tracking, the cell tracking module in NIS Elements was used to monitor single cell migration in time lapse images over 6 hours starting at ~12 hours into cell culture experiments. During quantification, migration was classified as a single cell that migrated more than an average distance of 2 nuclei and did not divide or interact with other cells. Statistical analysis of all data sets was performed using a two-tailed student's t-test, where $p<0.05$ is used to denote statistical significance.

Figure 2:
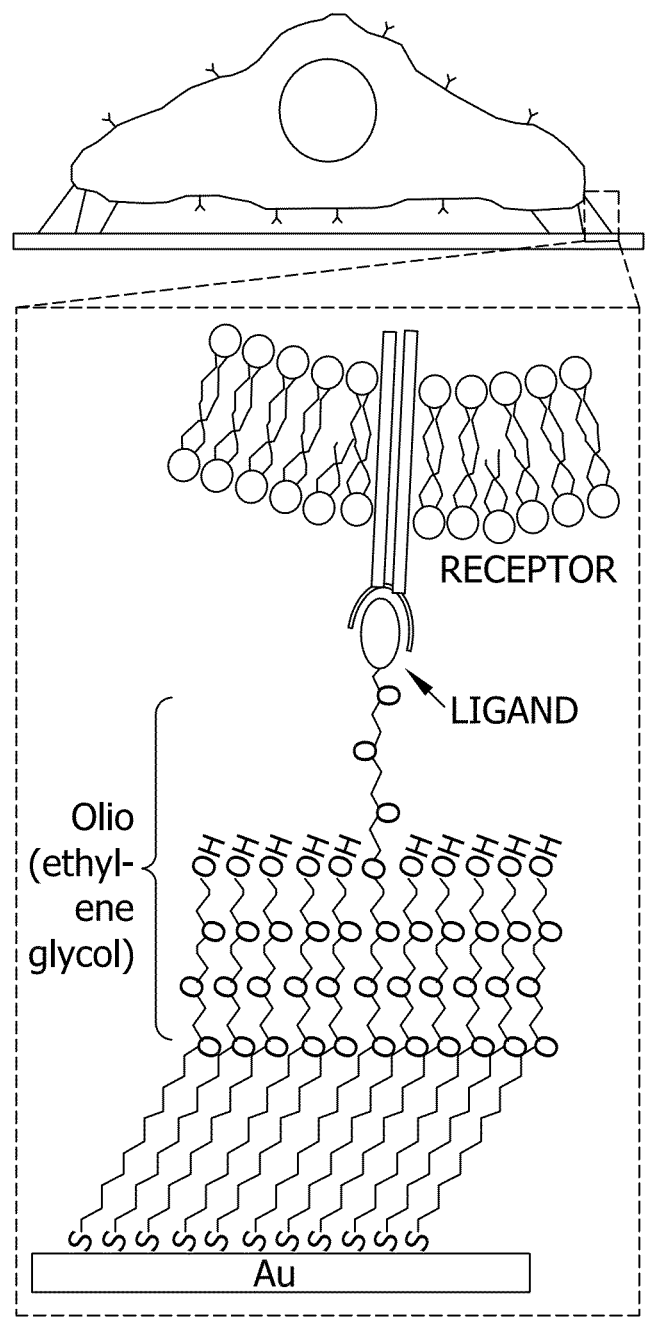
FIG. 2 is a schematic illustrating a ligand covalently attached to an oligo(ethylene glycol) of a SAM array spot interacting with a receptor on the surface of a cell.
Figure 3:
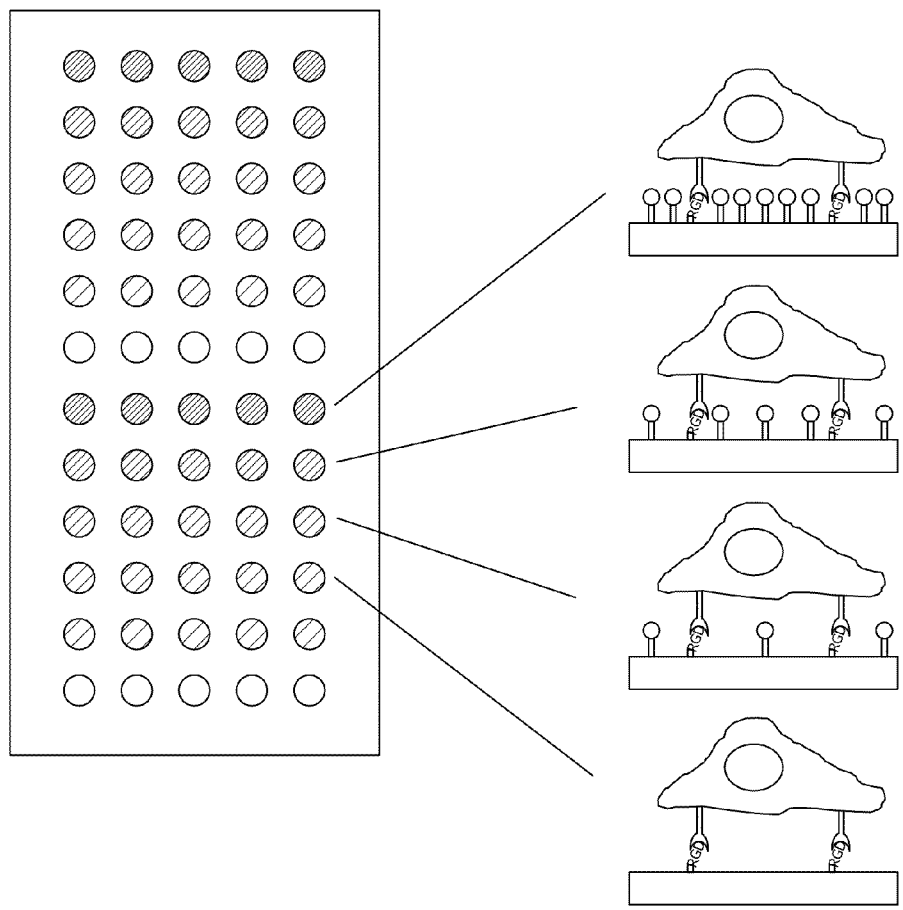
FIG. 3 is a schematic illustrating the design of SAM array spots to present conditions with controlled ligand (e.g., RGD) density as discussed in Example 1.
Figure 4A:
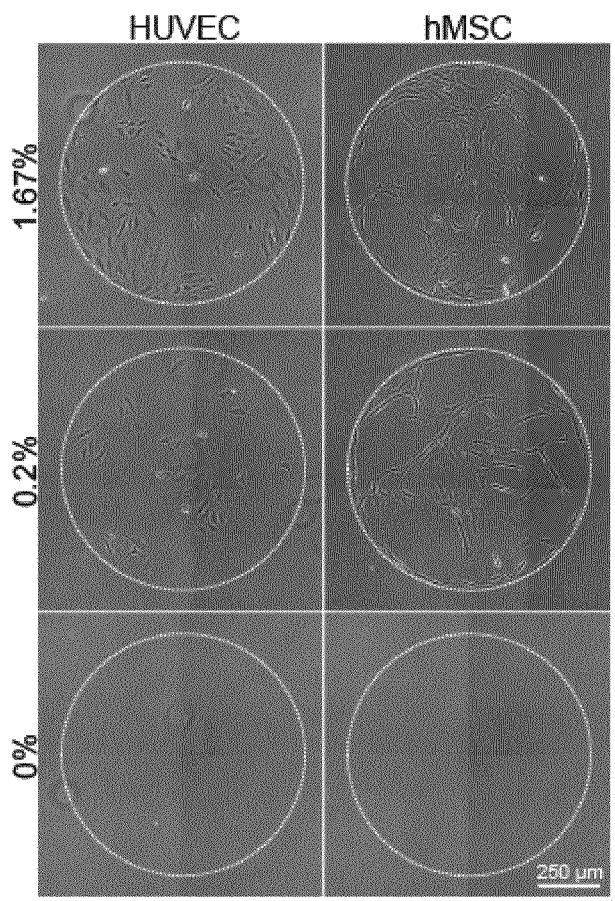
FIG. 4A shows phase contrast images of human umbilical vein endothelial cells (HUVEC) human mesenchymal stem cells (hMSC) cultured on SAM array spots presenting varied ligand densities as discussed in Example 1.

As illustrated in FIGS. 2 and 3, surface receptors on the cells specifically interact with the ligand on the SAM spot and not with the alkanethiolate. As shown in FIG. 4A, the density of HUVECs and hMSCs cultured on SAMs increased as the density of the ligand increased from 0% to 1.67%. Thus, cell attachment was ligand-dependent and showed similar responses to changes in ligand density. These results further demonstrate that the SAM arrays of the present disclosure allow for the ability to probe a wide range of ligand densities using identical substrate conditions, and thus, allowed for the identification of previously unreported similarities in the mechanisms controlling the initial attachment of HUVEC and hMSC primary cell types to culture surfaces.

Figure 4B:
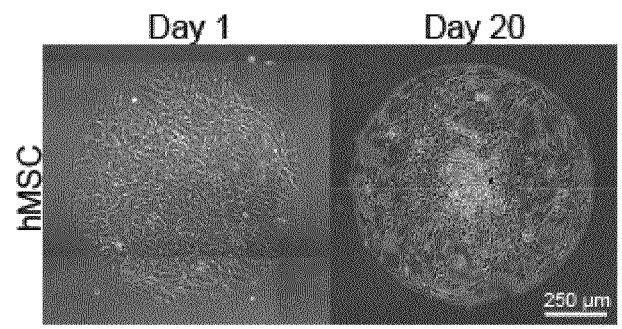
FIG. 4B shows phase contrast images of hMSCs cultured on SAM array spots for 1 day and 20 days as discussed in Example 1.

Moreover, in long term studies in which hMSCs were grown for 20 days with repeated media exchange, the cells remained confined within the ligand presenting spots (see, FIG. 4B). These results demonstrate that the SAM arrays of the present disclosure may be used to probe for ligand-specific effects on cell behavior in long-term studies.

Example 2

In this Example, cell attachment to SAM arrays presenting varied ligand densities was determined.

Specifically, SAM arrays were prepared as described above. HUVEC and hMSC were seeded onto SAM arrays presenting GRGDSP (SEQ ID NO:18) densities for 1 hour and rinsed to remove unattached cells. Following an incubation period of 1 hour to allow cells to attach, the SAM arrays were washed to remove unattached cells. Attached cells were immunofluorescently stained using FITC-anti-vinculin, TRITC-phalloidin, and DAPI. Cell morphology using SAM arrays presenting varied ligand densities was screened by culturing HUVECs and hMSCs for 24 hours on SAM arrays and stained for focal adhesion complexes and cytoskeletal organization. Cell spreading was determined by culturing HUVECs and hMSCs for 24 hours and 72 hours and analyzed by cell staining and quantified by measuring projected cell area.

Figure 5A:
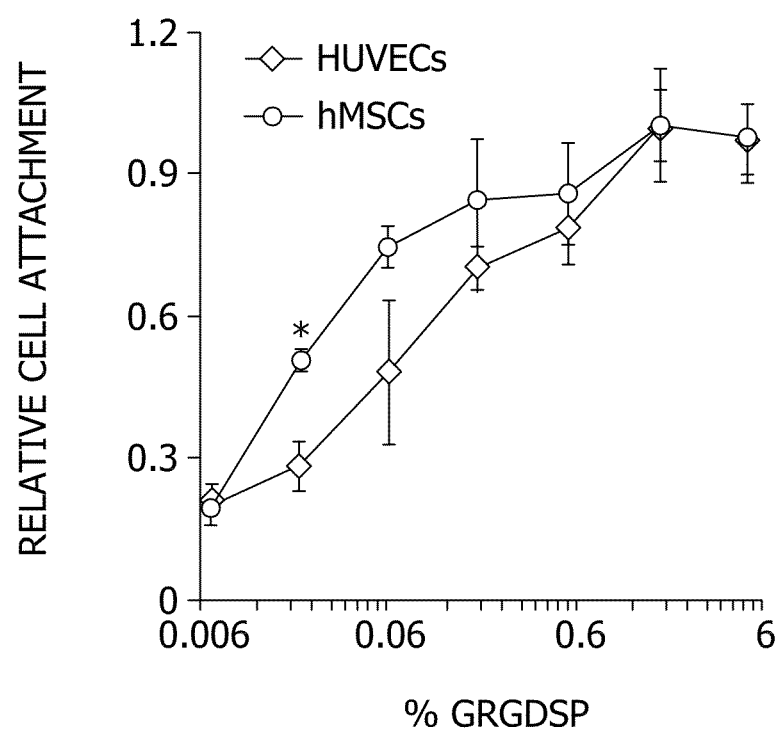
FIG. 5A is a graph illustrating HUVEC and hMSC attachment to SAM array spots presenting increased ligand densities after 1 hour as discussed in Example 2 (Error bars indicate standard error of the mean. Asterisk indicates significant increase in hMSC attachment compared to HUVEC attachment at the same ligand density.).
Figure 5B:
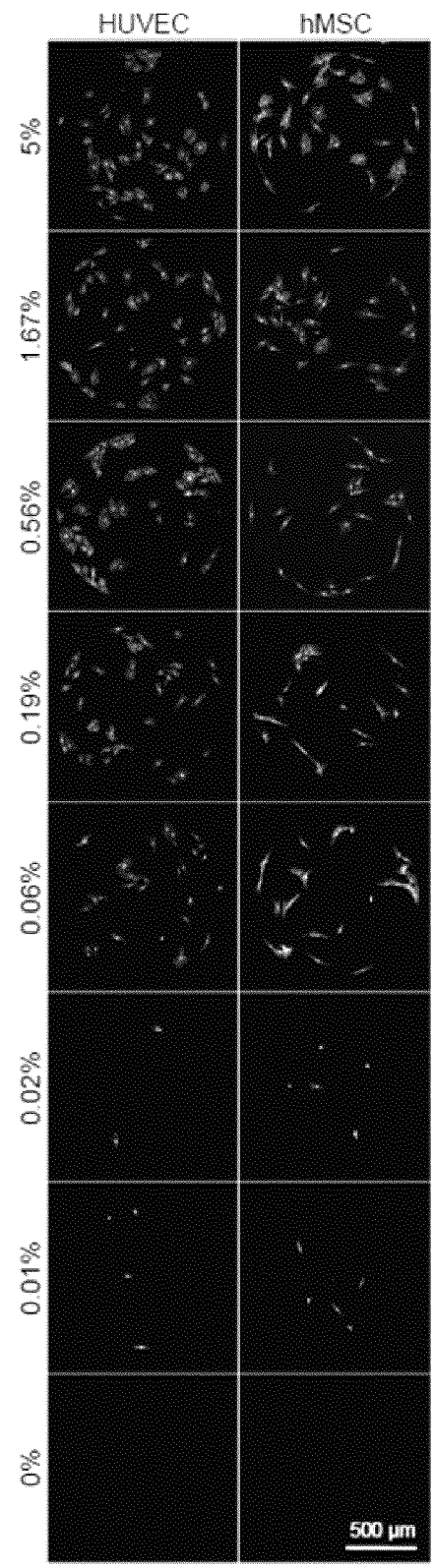
FIG. 5B shows immunofluorescent images showing HUVEC and hMSC attachment to SAM array spots presenting increased ligand densities after 24 hours as discussed in Example 2.

As shown in FIG. 5A, cell attachment of both HUVECs and hMSCs increased as the percent of ligand density increased. Immunofluorescent staining of cells on SAM arrays confirmed these results (see, FIG. 5B).

Figure 6:
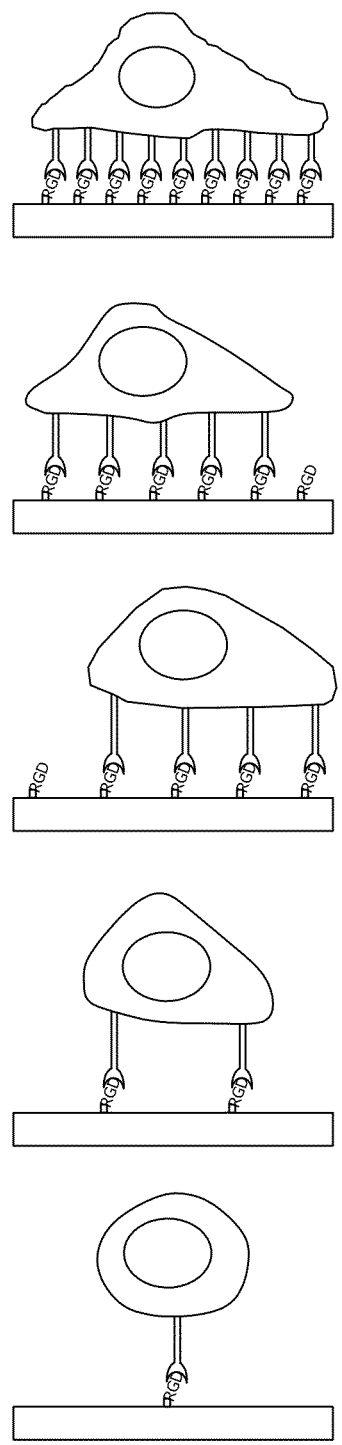
FIG. 6 is a schematic illustrating the effect of ligand density on cell morphology of cells cultured on SAM array spots with varied ligand densities as discussed in Example 2.

As illustrated in FIG. 6, cells form more contacts with the substrate and adopt a flatter and more spread morphology on SAM arrays spots having higher ligand densities as compared to cells cultured on SAM arrays spots having lower ligand densities. At lower ligand densities, cells form fewer contacts with the substrate and adopt a more rounded morphology.

Figure 7:
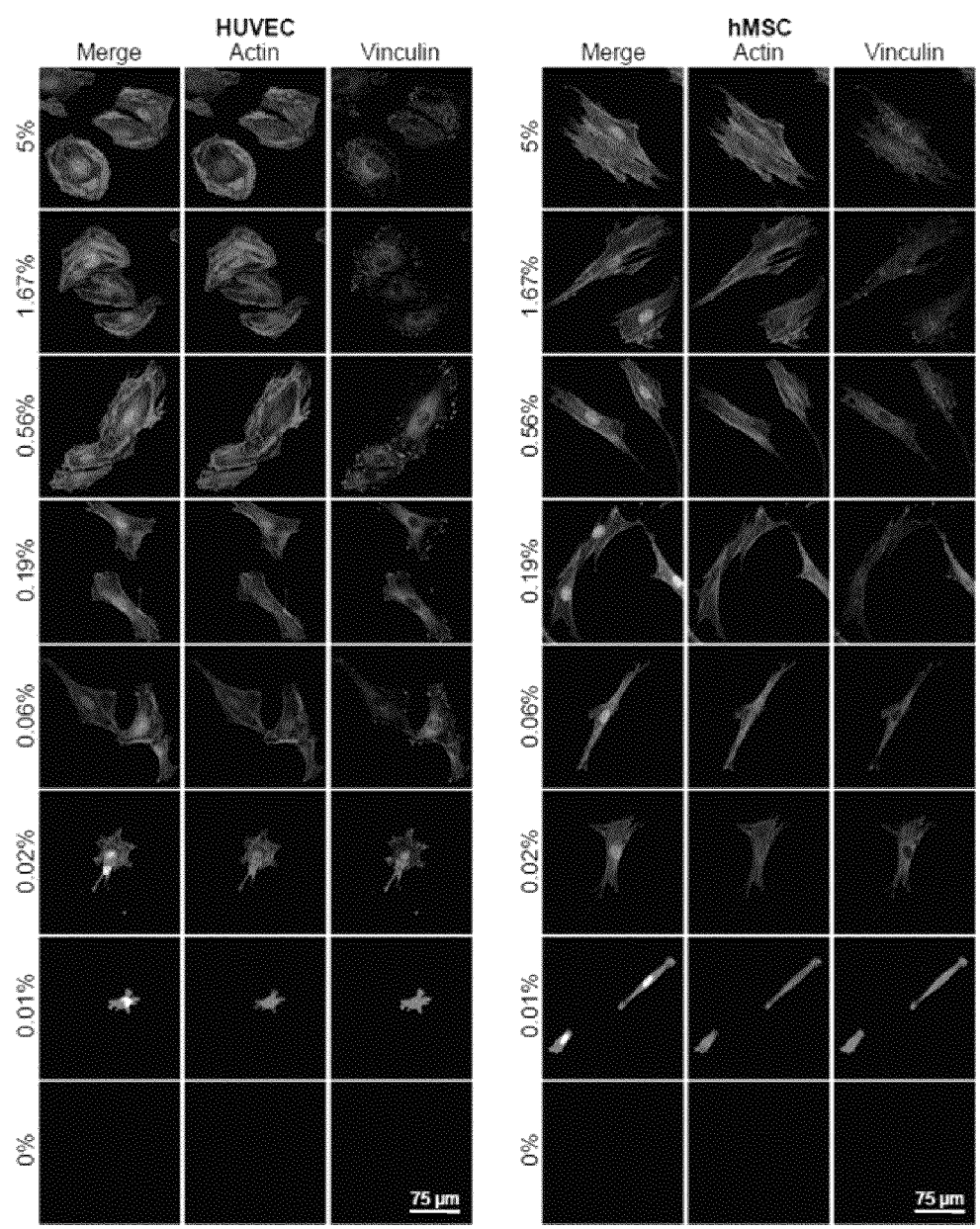
FIG. 7 shows immunofluorescent micrographs showing the effect of ligand density on cell morphology and structure of HUVECs and hMSCs cultured on SAM array spots presenting varied densities of ligand as discussed in Example 2.

As shown in FIG. 7, HUVECs and hMSCs developed unique cytoskeletal structure and focal adhesion organization at each ligand density after 24 hours of culture. Specifically, at high ligand densities, HUVECs expressed thick f-actin stress fibers terminated by focal adhesions prominently around the cell perimeter, whereas hMSCs were more elongated and fibroblastic, with f-actin stress fibers running longitudinally (parallel to the long axis of the cell) through the cell and terminated by focal adhesions. As ligand density was decreased, HUVECs became more elongated (FIG. 7, 0.19%, 0.06% GRGDSP (SEQ ID NO:18)) with stress fibers taking on a more longitudinal orientation and focal adhesions occurring on the ends of the elongated cell body. Changes for hMSCs were more subtle over the intermediate GRGDSP (SEQ ID NO:18) densities, with hMSCs maintaining an elongated shape and longitudinal stress fiber orientation but adopting a more spindle-shaped morphology. At the lowest GRGDSP (SEQ ID NO:18) density (FIG. 7, 0.01% GRGDSP (SEQ ID NO:18)), HUVECs and hMSCs both became morphologically compact with highly condensed f-actin and vinculin staining throughout the cell that made structure difficult to distinguish. At intermediate GRGDSP (SEQ ID NO:18) densities particular similarities in morphology and structure between hMSCs and HUVECs (e.g. HUVECs at 0.19% and hMSCs at 0.56%) were identified, which is in stark contrast to observations from high ligand density conditions (5%) or standard culture of these cell types.

Figure 8:
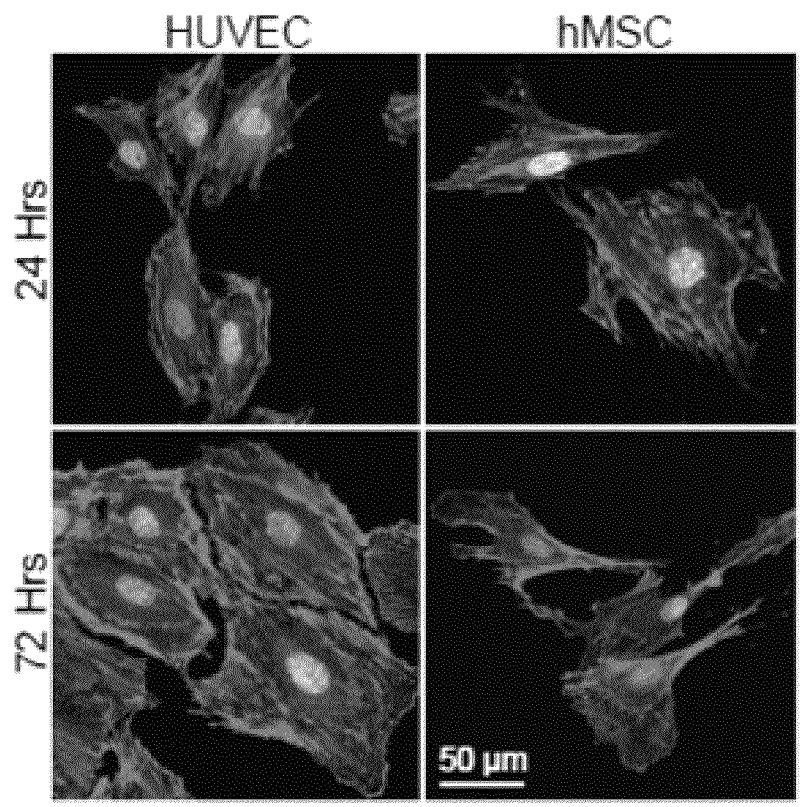
FIG. 8 shows immunofluorescent micrographs of cell spreading of HUVECs and hMSCs cultured on SAM array spots presenting 5% adhesion ligand at 24 and 72 hours as discussed in Example 2.
Figure 9A:
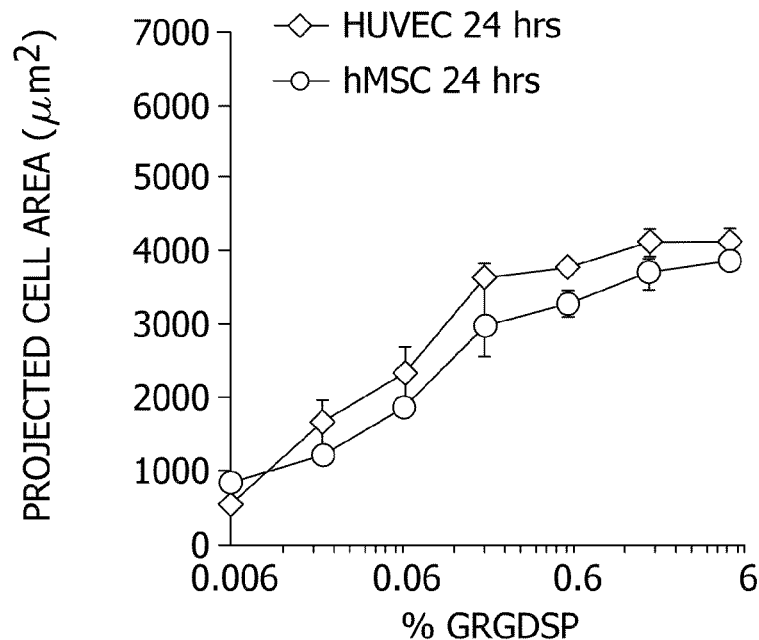
FIGS. 9A-9B are graphs illustrating projected cell areas between (A) HUVECs and (B) hMSCs cultured for 24 hours and 72 hours on SAM array spots as discussed in Example 2.
Figure 9B:
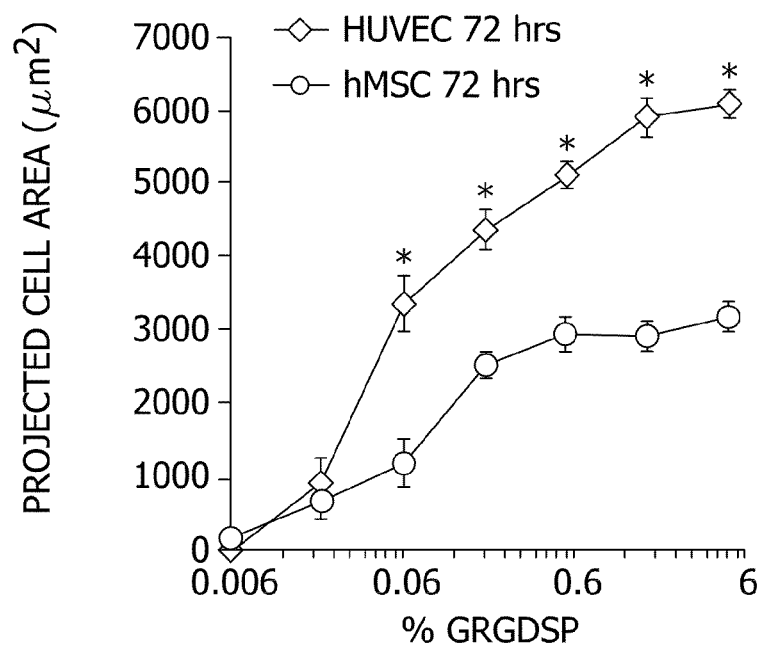

Projected cell area was not significantly different for HUVECs and hMSCs at 24 hrs for any of the conditions investigated, with maximal projected cell areas of greater than 4000 µm² occurring at 1.6% and 5% GRGDSP (SEQ ID NO:18) (FIG. 8 and FIGS. 9A and 9B). Both cell types exhibited ligand density-dependent changes in spreading. Taken together, these spreading results and the initial attachment results (FIG. 5A) highlight that, despite differences in cytoskeletal and adhesion component structures (FIG. 7), the two different cell types had remarkably similar attachment and spreading.

Figure 10A:
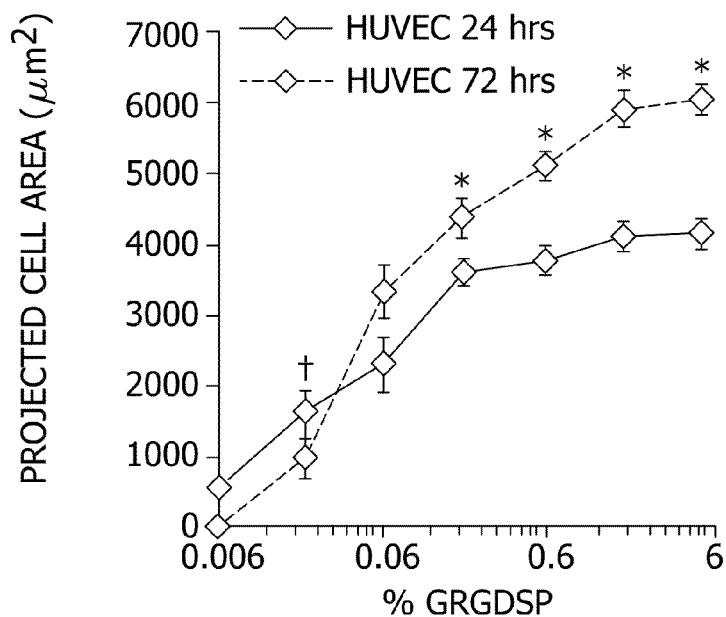
FIGS. 10A-10C are graphs illustrating projected cell areas within (A) HUVECs cultured for 24 hours and 72 hours and (B) hMSCs cultured for 24 hours and 72 hours and (C) relative spreading for each cell type and time point on SAM array spots as discussed in Example 2 (Error bars indicate standard error of the mean. Asterisk indicates significant increase in hMSC attachment compared to HUVEC attachment at the same ligand density.).
Figure 10B:
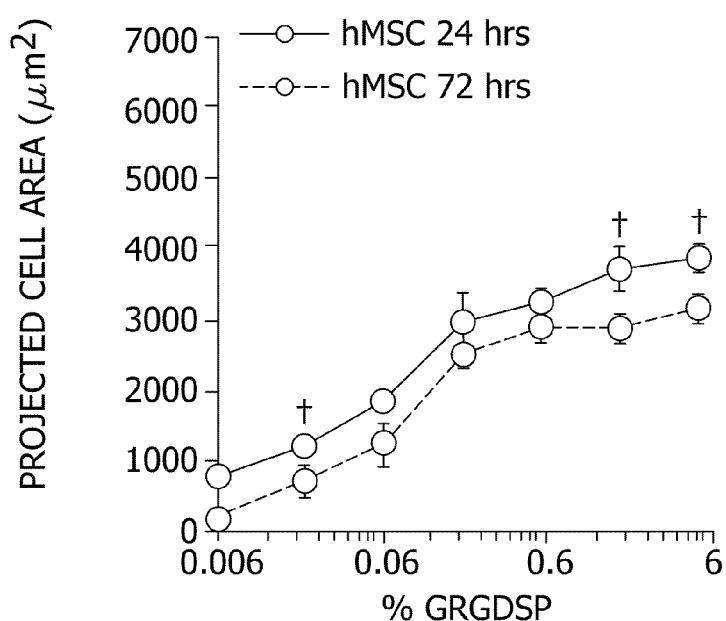
Figure 10C:
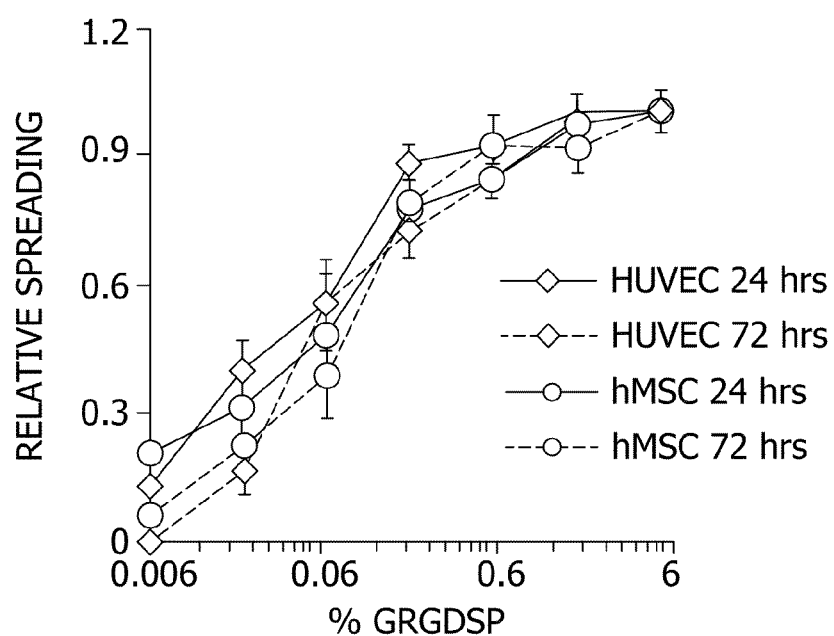

While spreading at 24 hrs was similar for HUVECs and hMSCs, changes in spreading differed markedly for the two cell types from 24 to 72 hrs in culture (FIG. 9B), with HUVECs increasing their projected cell area for all GRGDSP (SEQ ID NO:18) densities above 0.06% (FIG. 10A) and hMSCs projected area either decreasing or remaining constant with increasing ligand density (FIG. 10B). However, at 72 hours maximal HUVEC spreading reaching 6000 µm² was observed on 1.67% and 5% GRGDSP (SEQ ID NO:18) as well as a general increase in spreading across several ligand densities. Conversely, slight decreases in hMSC projected cell areas were observed from 24 to 72 hrs across several GRGDSP (SEQ ID NO:18) densities (FIG. 10B). These data suggest that it may be desirable to track cell adhesion over greater than 24 hours to understand the dynamics of cell phenotype, as cell spreading has been correlated to changes in differentiated function of both HUVECs and hMSCs. Interestingly, even with temporal changes in spreading, the relative spreading was almost identical for both cell types at both 24 and 72 hrs (FIG. 10C). Therefore, while these results indicate that temporal changes extend beyond timeframes typically used to characterize cell spreading, they also suggest that cell behavior maintains a similar dependence on ligand density over time.

Example 3

In this Example, the influence of systematic changes in ligand density for HUVECs compared to hMSCs was determined using SAM arrays to further characterize cell adhesion-dependent influences on cell proliferation behavior.

Figure 11:
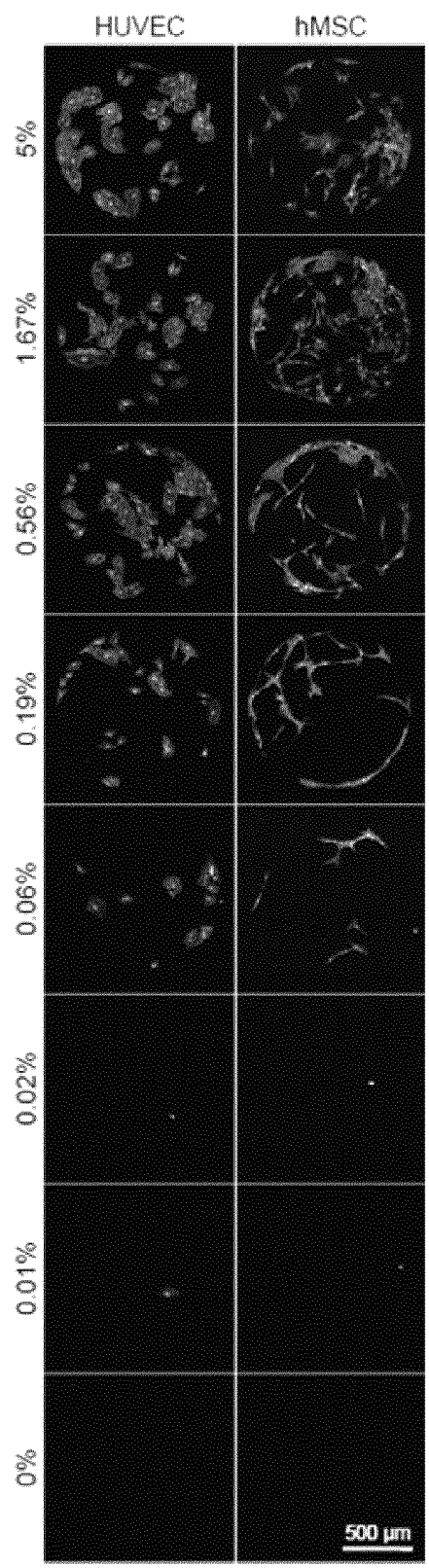
FIG. 11 shows immunofluorescent micrographs of HUVEC and hMSC proliferation at 72 hours in culture on SAM array spots presenting 0% to 5% ligand densities as discussed in Example 3.

Proliferation was quantified by normalizing the cell number at 72 hours ($C_{72}$) to the number of cells at 0 hr ($C_0$). Based on this notation, normalized cell numbers greater than one ($C_{72}/C_0>1$) indicate proliferation and values less than one ($C_{72}/C_0<1$) indicate cell death or detachment. Relative proliferation over 72 hours for each cell type was determined by scaling proliferation at each condition to maximum proliferation and was also compared to relative spreading at 24 hours (Error bars indicate standard error of the mean. Asterisk indicates significant difference between HUVECs and hMSCs at a specific adhesion ligand density $p<0.05$). Cells were stained for fixed and stained for vinculin, actin and nuclei at 72 hours (FIG. 11). Cell migration using SAM arrays was determined by imaging SAM arrays seeded with HUVECs and hMSCs every 15 minutes using automated microscopy and tracking over 12-18 hours (FIG. 13).

Figure 12A:
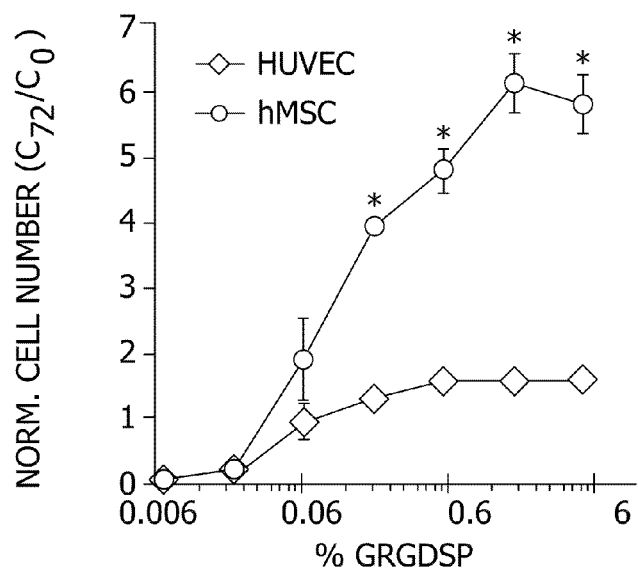
FIGS. 12A-12C are graphs quantifying proliferation of (A) HUVECs and (B) hMSCs and (C) relating relative proliferation to relative spreading over 72 hours for each cell type on SAM array spots presenting 0% to 5% ligand densities as discussed in Example 3 (Error bars indicate standard error of the mean. Asterisk indicates significant difference between HUVECs and hMSCs at the same ligand density.).
Figure 12B:
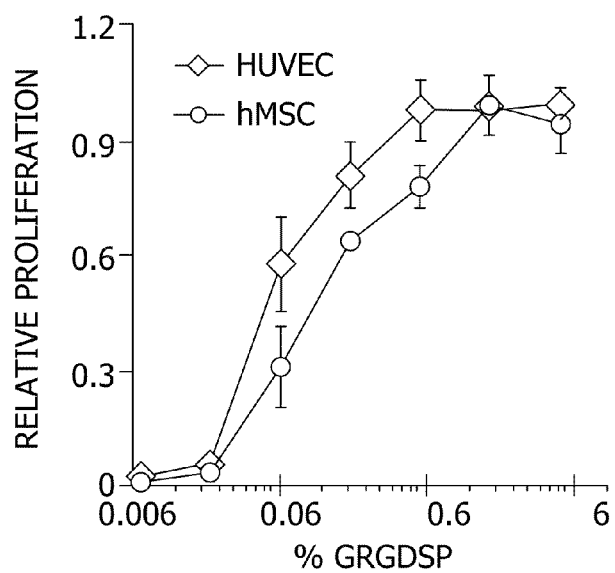
Figure 12C:
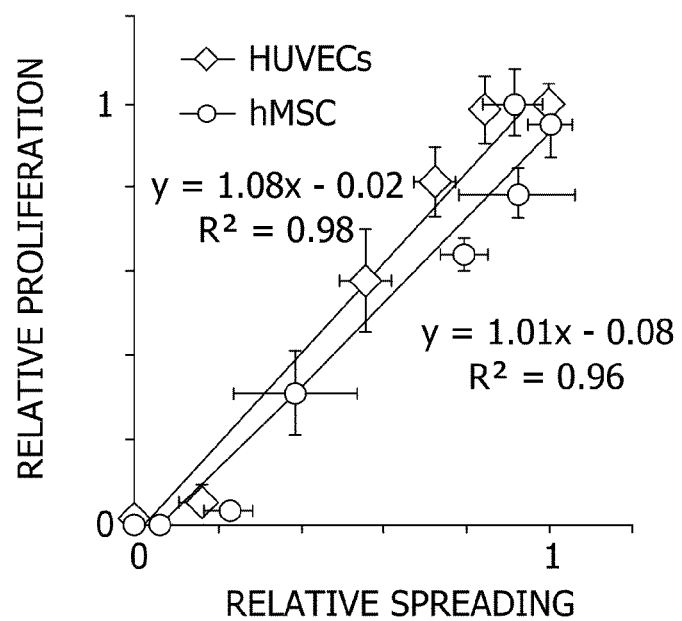

Cell types exhibited different proliferation rates with HUVECs achieving a maximum normalized cell number of 1.6 and hMSCs achieving a maximum of 6.1. Despite these differences in maximum proliferation, proliferation as a function of ligand density was similar for both HUVECs (FIG. 12A) and hMSCs (FIG. 12B) with increasing proliferation over GRGDSP (SEQ ID NO:18) densities ≥0.06% and no proliferation below 0.06% GRGDSP (SEQ ID NO:18). Furthermore, calculation of relative proliferation depicts statistically identical proliferative responses to adhesion ligand density (FIG. 12C). Both cell types exhibited similar adhesion ligand dependencies for proliferation. Importantly, these results demonstrate that through a well-controlled comparison, adhesion dependence on proliferation was identical for two distinct cell types over a wide range of ligand densities.

Although HUVEC and hMSC spreading and proliferation trends over 72 hrs were similar, stark differences in migration morphology and relative number of migrating cells as a function of cell adhesion were observed. FIGS. 13A and 13B show images of HUVECs and hMSCs migrating on SAM arrays presenting 5% ligand (FIG. 13A) and 0.06% (FIG. 13B). Single cell tracking was used to quantify the percentage of cells migrating on SAM arrays in each condition (Error bars indicate standard error of the mean. Asterisk indicates significant increase in HUVEC migration compared to all of their adhesion ligand conditions and "NS" indicates no significant difference between cell types at a single adhesion ligand density, $p<0.05$).

Figure 14:
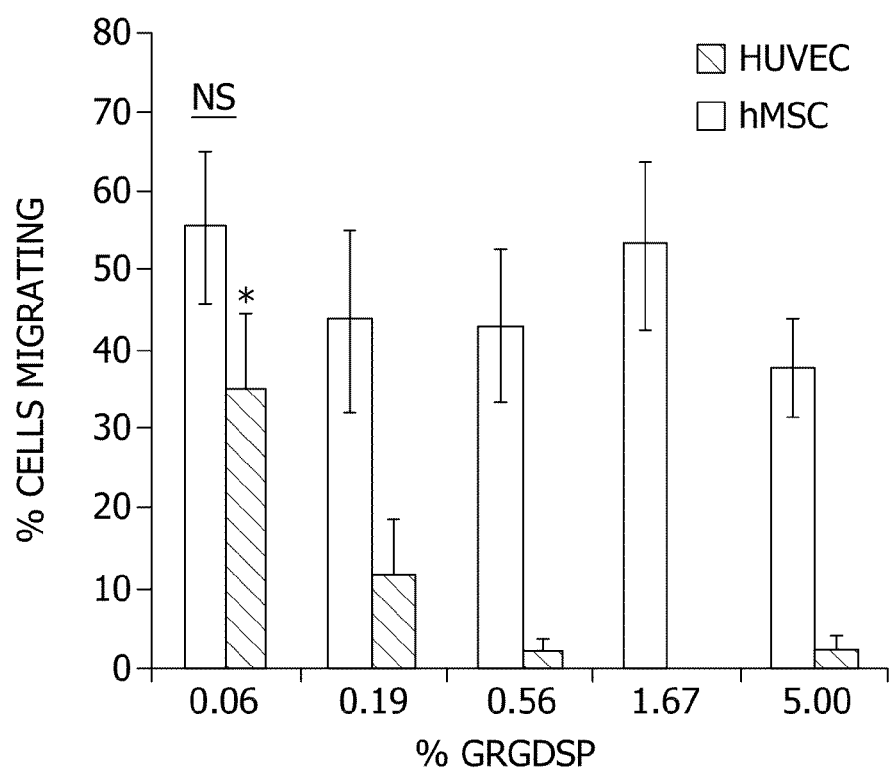
FIG. 14 is a graph quantifying percentage of cells migrating on SAM array spots presenting 0.06%-5% ligand as discussed in Example 4 (Error bars indicate standard error of the mean. Asterisk indicates significant increase in HUVEC migration compared to all other ligand conditions and "NS" indicates no significant difference between cell types at the same ligand density, $p<0.05$.).

The fraction of migrating hMSCs was insensitive to ligand densities with greater than 37% of the cell migrating for each condition (FIG. 13C). In contrast, HUVEC migration was highly dependent on ligand density with virtually no cells migrating on high GRGDSP (SEQ ID NO:18) densities but over 30% of the cells migrating at lower GRGDSP (SEQ ID NO:18) densities. The morphology of migrating cells was also a function of ligand density (FIGS. 13A and 14B). HUVECs exhibited static behavior on 5% GRGDSP (SEQ ID NO:18) in which the cell body continuously oscillated, but little net movement was observed. In contrast, hMSCs migrating on high GRGDSP (SEQ ID NO:18) densities exhibited migratory phenotypes characterized by polarized membranes with leading edges driven by active membrane protrusions such as lammellipodia and filopodia, consistent with phenotypes of migrating fibroblasts. At lower densities of ligand, both cell types exhibit migratory phenotypes that were similar to hMSC behavior on 5% GRGDSP (SEQ ID NO:18) (polarized cell body with leading edge protrusions) but had subtle differences. hMSCs on high densities of ligand concertedly progressed through the following steps of migration: i) protrusion of the leading edge, ii) attachment to the surface, iii) contraction of the cytoplasm, and iv) release and retraction of the rear end. hMSC and HUVEC migration on low ligand densities also followed these steps of migration, but each step was more clearly defined giving the cells a more sporadic migration appearance (FIG. 13B). These results suggest a potential adhesion-dependent role for protrusion dynamics, with more fan or sheet-like protrusions (lammellipodia) at high ligand densities, but more pronounced spike-like protrusions (filopodia) at low ligand density.

Example 4

In this Example, SAM arrays were used to culture different cell types.

Specifically, SAM arrays were prepared as discussed above and seeded with human dermal fibroblasts (hDF), human fibrosarcoma cells (HT-1080s) and human embryonic stem cells (hESCs).

Figure 15:
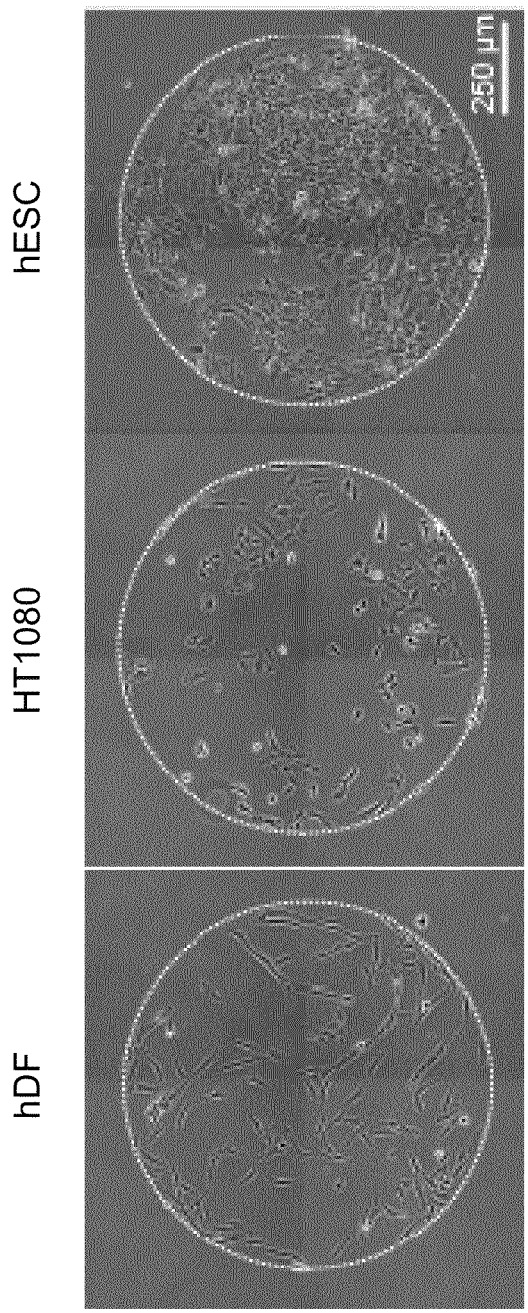
FIG. 15 shows phase contrast images of human dermal fibroblasts (hDF), human fibrosarcoma cells (HT-1080's) and human embryonic stem cells (hESCs) cultured on SAM array spots presenting ligand as discussed in Example 4.

As shown in FIG. 15, hDF (FIG. 15A), HT-1080s (FIG. 15B) and hESCs (FIG. 15C) all attached and proliferated on SAM arrays. Thus, the SAM array platform of the present disclosure affords enhanced throughput experimental methodologies that not only enable screening a large set of experimental variables, but also direct comparison of multiple cell types. In addition to the carbodiimide chemistries used in this work for ligand immobilization, the SAM array fabrication process described herein may also be amenable to other immobilization chemistries such as, for example, copper catalyzed azide-alkyne cycloadditions, which offers several strategies for immobilization of a range of different ligands (e.g., peptides, nucleic acids, and polysaccharides).

Example 5

In this Example, cell attachment to SAM arrays presenting varied ligand densities and combinations of bone morphogenetic protein receptor-binding peptide (BR-BP) and heparin proteoglycan-binding peptide (HPG-BP) was determined.

Figure 16:
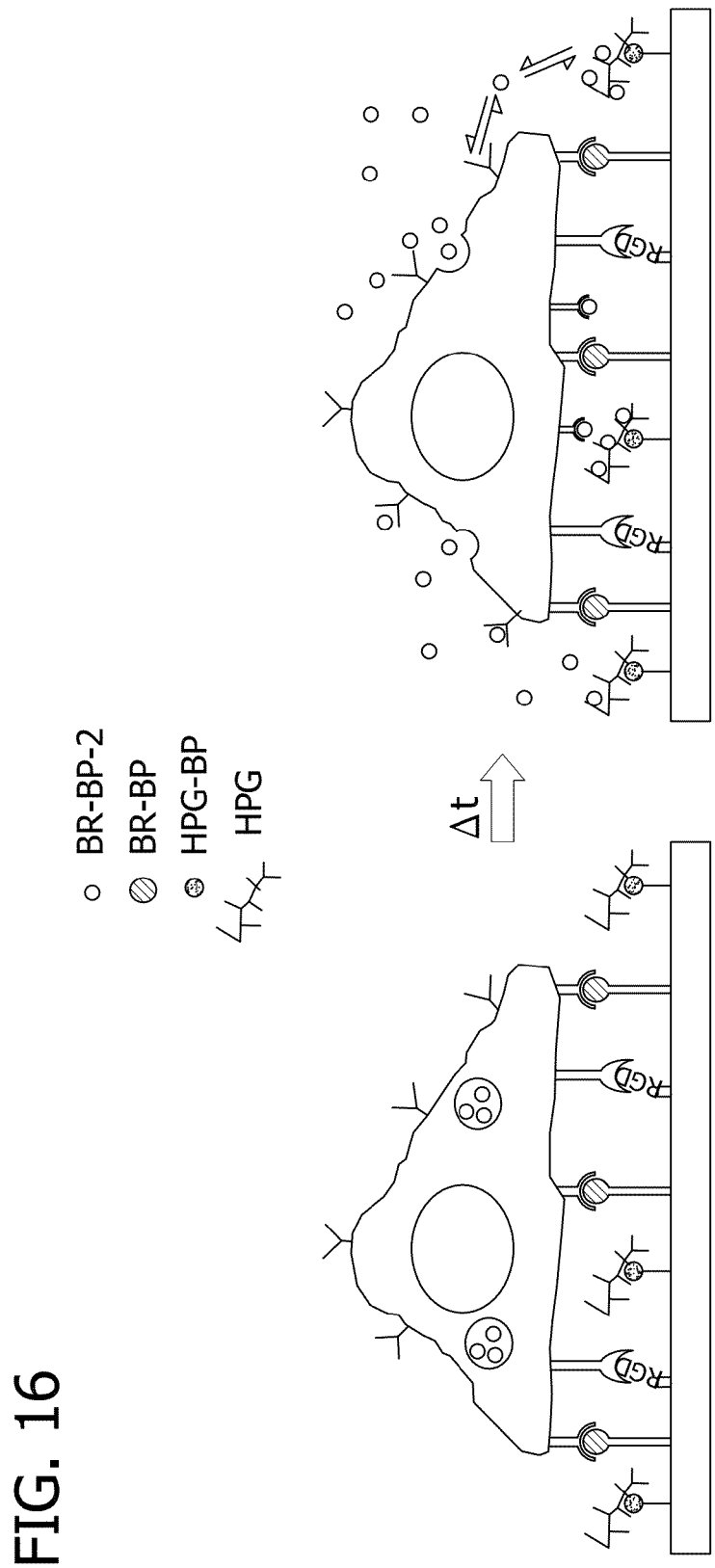
FIG. 16 is a schematic illustrating osteogenesis on a SAM array spot presenting both BMP-2 receptor-binding peptide and heparin proteoglycan-binding peptide as discussed in Example 5.

As illustrated in FIG. 16, BR-BP may stimulate hMSC production and release of osteogenic factors such as soluble BMP-2, which is then sequestered and localized in the pericellular environment by surface-bound heparin proteoglycans (HPG), which further stimulates osteogenesis. As illustrated in FIG. 17, SAM arrays were prepared as described above with high, medium and low GRGDSP (SEQ ID NO:18) densities and BR-BP+HPG-BP, BR-BP+HPG-BP scramble, HPG-BP+BR-BP scramble, and BR-BP scramble+HPG-BP scramble control peptides. In this SAM array approach, each spot was designed to contain the same total molar density (mol/cm$^2$) of peptide from spot to spot. Therefore, control over individual peptide density was achieved by mixing scrambled BR-BP and HPG-BP and mutant GRGESP (SEQ ID NO:19) peptides with functional BR-BP, HPG-BP or GRGDSP (SEQ ID NO:18) peptides, respectively. Therefore, in a typical SAM array, SAMs were locally formed within spots using an alkanethiolate mixture of 95% HS—$C_{11}$-$EG_3$-OH and 5% HS—$C_{11}$-$EG_6$-COOH to create substrates with a total of 5% carboxylate groups for peptide conjugation. Here, "X %" refers to the mole percent of alkanethiolate present during SAM formation and subsequently the approximate amount of an alkanethiolate present on the surface after SAM formation. To regulate the density of active peptide present in each spot, mutant and scramble versions of peptides were included during peptide conjugation. Therefore, to create a spot presenting a "high" density of GRGDSP (SEQ ID NO:18) with BR-BP and HPG-BP 100 μM peptide solution with 50 μM GRGDSP (SEQ ID NO:18), 25 μM BR-BP, and 25 μM HPG-BP was used during peptide conjugation to generate a spot with 2.5% GRGDSP (SEQ ID NO:18), 1.25% BR-BP, and 1.25% HPG-BP. Likewise, to create a spot presenting a "low" density of GRGDSP (SEQ ID NO:18) and BR-BP, a 5.5 μM GRGDSP (SEQ ID NO:18), 44.4 μM GRGESP (SEQ ID NO:19), 25 μM BR-BP, and 25 μM scrambled HPG-BP was used during peptide conjugation. In these experiments, high, medium, and low GRGDSP (SEQ ID NO:18) densities correspond to 2.50%, 0.83%, and 0.27% GRGDSP (SEQ ID NO:18) with 0%, 1.67%, and 2.23% GRGESP (SEQ ID NO:19). In this manner, the amount of active peptide was varied between spots while total peptide content was held constant. As mentioned previously, peptide concentrations were easily measured using UV/Vis since all peptides either contained residues that absorbed strongly at 280 nm, or were engineered to contain tryptophan residues in the poly-glycine tail. Cells were added at a density of 50,000 cells/cm$^2$ and cultured for 5 days. During hMSC expansion and experiments on SAM arrays performed in "growth medium" (GM), hMSCs were cultured in low glucose Dulbecco's Modified Eagles Medium supplemented with 10% Fetal Bovine Serum (Atlanta Biologicals, Lawerenceville Ga.) and Penicillin (10000 IU/ml)/Streptomycin (10000 μg/ml)/Amphotericin B (25 μg/ml) antibiotic (CellGro, MediaTech, Manassas, Va.). For conditions performed in "osteogenic medium" (OM), hMSCs on SAM arrays were cultured in growth medium supplemented with 1% beta-glycerolphosphate, 0.1% ascorbic acid, 0.01% dexamethasone (Sigma, St. Louis, Mo.), and 0.01 μM vitamin D3 (Enzo Life Science, Farmingdale, N.Y.).

Example 6

In this Example, cell surface coverage over time was determined.

Specifically, SAM arrays presenting low, medium and high GRGDSP (SEQ ID NO:18) and BR-BP+HPG-BP, BR-BP+HPG-BP scrambled, HPG-BP+BR-BP scrambled, and BR-BP scrambled+HPG-BP scrambled peptides were prepared as described above. hMSCs were seeded on SAM array spots at confluence (50,000 cells/cm$^2$) and imaged out to 20 days.

Figure 19A:
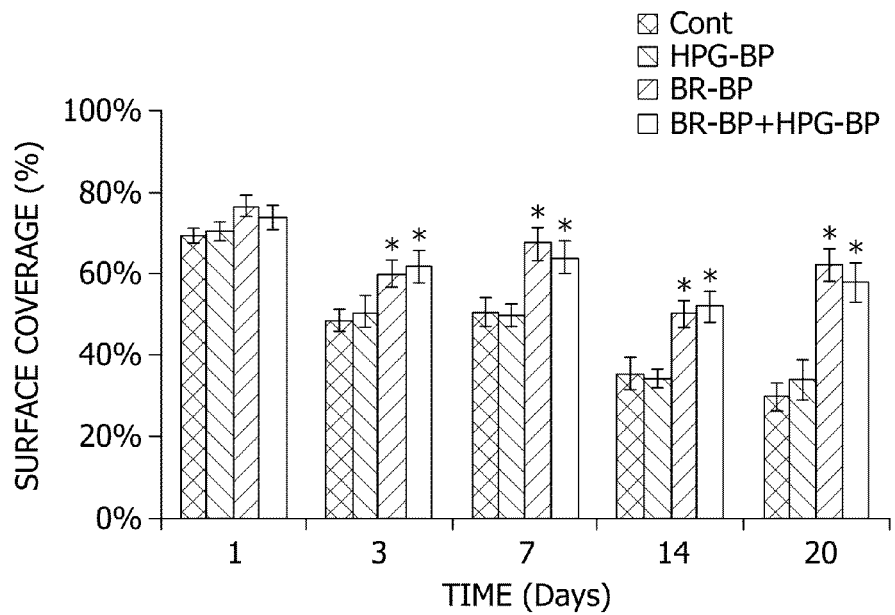
FIGS. 19A and 19B are graphs illustrating hMSC surface coverage on SAM array spots presenting variable ligand densities with combinations of BR-BP and HPG-BP peptides and cultured in (A) growth medium and (B) osteogenic medium over time as discussed in Example 6.
Figure 19B:
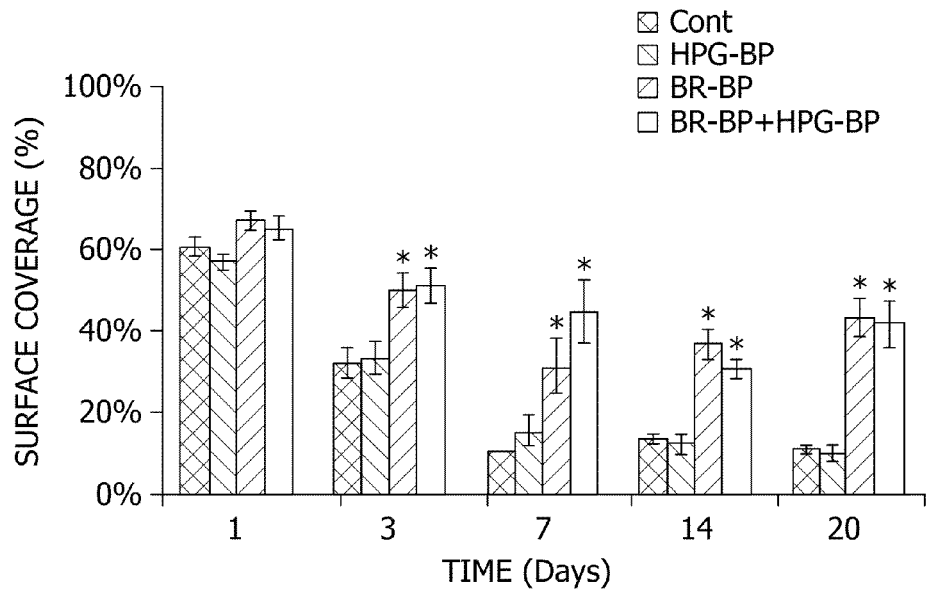

As shown in FIGS. 18A-18C and quantified in FIGS. 19A and 19B, cells cultured for 20 days on SAM spots presenting high ligand density promoted cell survival. Moreover, BR-BP+HPG-BP or BR-BP alone maintained hMSC surface coverage on low GRGDSP (SEQ ID NO:18) density SAM spots. The results presented in this example demonstrated that BR-BP promoted hMSC surface coverage over time in culture.

Example 7

In this Example, the influence of ligand on alkaline phosphatase activity in hMSCs cultured on SAM arrays presenting BR-BP+HPG-BP, BR-BP, HPG-BP, and Control (Cont) was determined.

hMSCs were seeded at 50,000 cells/cm$^2$ and cultured in either growth media or osteogenic media. After 7 days in culture, media were removed and then hMSCs on SAM arrays were rinsed with PBS and fixed via treatment with a 1% paraformaldehyde in PBS for 5 minutes. Cells were then stained with a BCIP/NBT alkaline phosphatase substrate kit (Vector Laboratories, Burlingame, Calif.) according to the manufacturer's protocol using a 1 hour incubation at room temperature. After staining, SAM arrays were rinsed with PBS and then imaged.

Figure 21A:
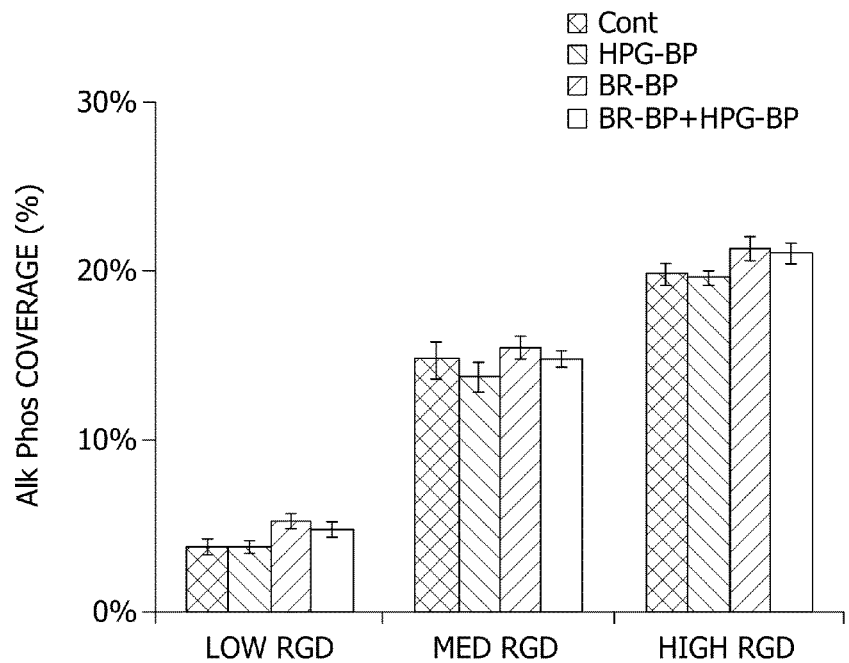
FIGS. 21A and 21B are graphs illustrating hMSC surface coverage on SAM array spots presenting variable ligand densities with combinations of BR-BP and HPG-BP peptides and cultured in (A) growth medium and (B) osteogenic medium over time as discussed in Example 7.
Figure 21B:
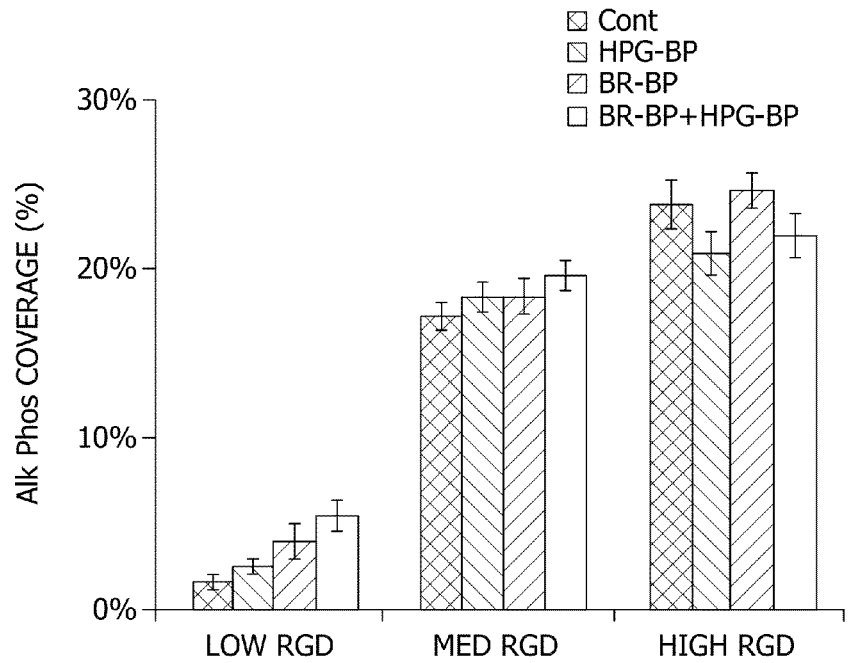

As shown in FIGS. 20A-20F, hMSCs cultured on SAM spots presenting high GRGDSP (SEQ ID NO:18) density exhibited increased staining for alkaline phosphatase activity. Alkaline phosphatase activity decreased with decreasing GRGDSP (SEQ ID NO:18) density. Additionally, cells cultured in osteogenic media demonstrated higher alkaline phosphatase activity levels. Quantification of the cell coverage of cells exhibiting alkaline phosphatase activity confirmed the visual results (See, FIGS. 21A and 21B).

The results demonstrated that the effect of GRGDSP (SEQ ID NO:18) density presented on SAM array spots dominated alkaline phosphatase expression with respect to BR-BP and HPG-BP peptides at day 7 of culture on SAM array spots.

Example 8

In this Example, the response of HUVECs cultured on SAM array spots presenting ligand to soluble morphogens was determined.

Specifically, SAM array spots presenting mixed ligands were prepared as described above. SAM arrays presenting varied ligand densities of covalently immobilized VEGF receptor-binding peptide (KLTWQELYQLKYKGI, here referred to as "VR-BP"; SEQ ID NO:17) and varied ligand densities of the fibronectin-derived cell adhesion peptide (GRGDSP, SEQ ID NO:18) were used to probe for changes in HUVEC attachment, proliferation and tubulogenesis. Control over individual ligand density was achieved by mixing scrambled VR-BP and mutant GRGESP (SEQ ID NO:19) with functional VR-BP or GRGDSP (SEQ ID NO:18) peptides, respectively. Therefore, in a typical SAM array, SAMs were locally formed within spots using an alkanethiolate mixture of 94% HS—$C_{11}$-$EG_3$-OH and 6% HS—$C_{11}$-$EG_6$-COOH to create substrates with a total of 6% carboxylate groups for peptide conjugation. Next, to create a spot presenting 5% GRGDSP (SEQ ID NO:18) and 1% VR-BP, a 300 µM peptide solution with 250 µM GRGDSP (SEQ ID NO:18) and 50 µM VR-BP was used during peptide conjugation. Likewise, to create a spot presenting 2.5% GRGDSP (SEQ ID NO:18) and 0.1% VR-BP, a 300 µM peptide solution with 125 µM GRGDSP (SEQ ID NO:18), 125 µM GRGESP (SEQ ID NO:19), 5 µM VR-BP and 45 µM scrambled peptide was used during peptide conjugation. In this manner, the amount of active ligand could be varied between spots while holding the total ligand content constant. As mentioned previously, ligand concentrations were measured using UV/Vis since all peptides either contained residues that absorbed strongly at 280 nm, or were engineered to contain tryptophan residues in the poly-glycine tail.

Passage 2 HUVECs were expanded at low cell density (less than 70% confluence) on tissue culture polystyrene to no more than 14 population doublings. During HUVEC expansion, cells were cultured in medium 199 (m199, Mediatech, Manassas, Va.) containing 1% penicillin/streptomycin (Hyclone, Logan, Utah) and supplemented with Clonetics EGM-2 BullitKit (Lonza Walkersville, Inc., Walkersville, Md.) containing Hydrocortisone, hFGF-B, VEGF, R3-IGF-1, Ascorbic Acid, Heparin, FBS, hEGF, GA-1000 growth supplements. NIH 3T3 cells were expanded in Dulbecco's modified eagles medium (DMEM, Mediatech, Manassas, Va.) containing 1% penicillin/streptomycin and supplemented with 5% cosmic calf serum (Hyclone, Logan, Utah). Before seeding on SAM arrays, HUVECs in cell culture flasks were starved for 24 hours in medium containing 2% FBS and then removed from the plate using a 0.05% trypsin solution and resuspended in m199 with 2% FBS. Cell suspension was seeded onto SAM arrays in sterile polystyrene Petri dishes and incubated in a humid environment at 37° C. and 5% $CO_2$. After allowing cells to attach for ~1 hr, arrays were dipped in warm m199 with 2% FBS to remove loosely attached cells and then transferred to a rectangular multidish (Thermo Scientific/Nunc, Rochester, N.Y.) containing warm media with 2% FBS and imaged ~2 hours later serving as "0 hr". After imaging, media was replaced with m199 with 2% FBS containing varied concentrations soluble molecules such as recombinant VEGF (VEGF-$A_{165}$, R&D systems, Minneapolis, Minn.) or VR-BP. For inhibition using SU5416, 10 µM SU5416 (Sigma-Aldrich, St. Louis, Mo.) was present during cell seeding and the 2 hours before imaging but was washed out before addition of VEGF conditions. NIH 3T3 experiments were performed using the same approach, in DMEM with 5% cosmic calf serum for all cases. To determine the influence of soluble peptide, HUVECs were seeded on SAM arrays with varied densities of GRGDSP and then cultured in m199 with 2% FBS containing no additional growth factor, 10 ng/ml VR-BP, or 10 ng/mL recombinant VEGF for 24 hours. To assess proliferation, a Click-it EdU assay (Invitrogen, Carlsbad, Calif.) was used to label HUVECs in S-phase as indicated by the manufacturer. Briefly, 5 µl of 10 mM EdU in DMSO (5-ethynyl-2'-deoxyuridine) was added to each well (to achieve a final concentration of 10 µM) and placed in an incubator. After 6 hours, HUVECs were fixed using 4% buffered formalin for 15 minutes, permeabilized using 0.5% Triton X-100 (MP Biomedicals, Aurora, Ohio) in PBS, and then exposed to a reaction cocktail containing a reactive Alexa Fluor 488 azide to fluorescently label synthesized DNA containing the EdU nucleotide. HUVEC nuclei were then counterstained using 10 ng/mL Hoechst 33342 in PBS for 10 minutes and then imaged to assess the fraction of HUVEC nuclei staining positive for EdU incorporation.

Figure 22:
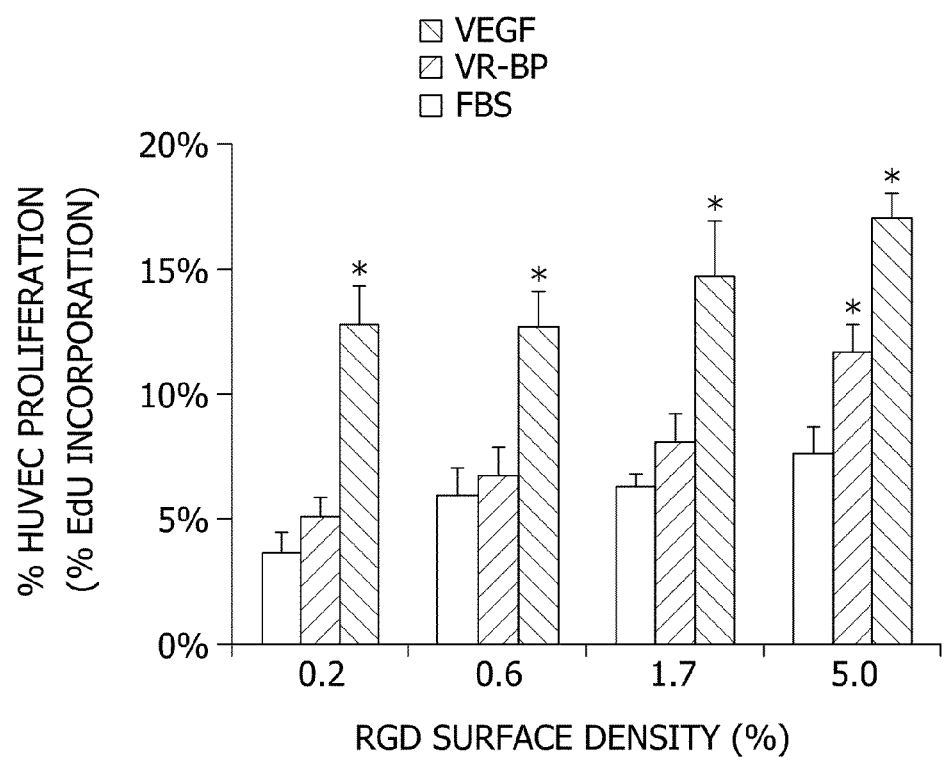
FIG. 22 is a graph illustrating the response of HUVECs to soluble morphogens cultured on SAM array spots presenting varied ligand densities in the presence of fetal bovine serum (FBS) alone or with the addition of VR-BP or VEGF as discussed in Example 8 (Error bars indicate standard error. Asterisk indicates significance compared to FBS alone, $p<0.05$.).

As shown in FIG. 22, HUVECs cultured on SAM arrays presenting the highest ligand density and stimulated with soluble VR-BP exhibited significant increases in proliferation compared to cells without stimulation. Similarly, soluble recombinant VEGF stimulated increased HUVEC proliferation that exceeded both untreated control conditions and soluble VR-BP conditions. HUVECs also exhibited a dependence on ligand (GRGDSP, SEQ ID NO:18) density, with increased proliferation correlating with increased ligand (GRGDSP, SEQ ID NO:18) density, whereas conditions presenting the mutant ligand (GRGESP, SEQ ID NO:19) did not promote HUVEC attachment, indicating that HUVEC-substrate interactions were confined to integrin-GRGDSP binding.

Example 9

In this Example, SAM arrays were prepared using multiple ligand mixtures.

Figure 23:
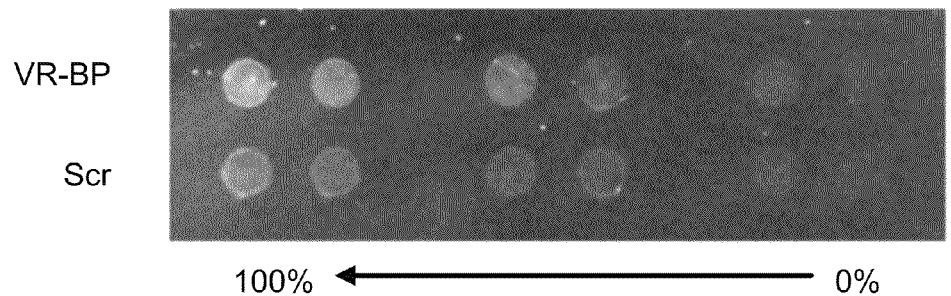
FIG. 23 is a fluorescent image showing detection of VR-BP peptide and scrambled peptide (Scr) mixed with ligand presented on SAM array spots as discussed in Example 9.
Figure 24:
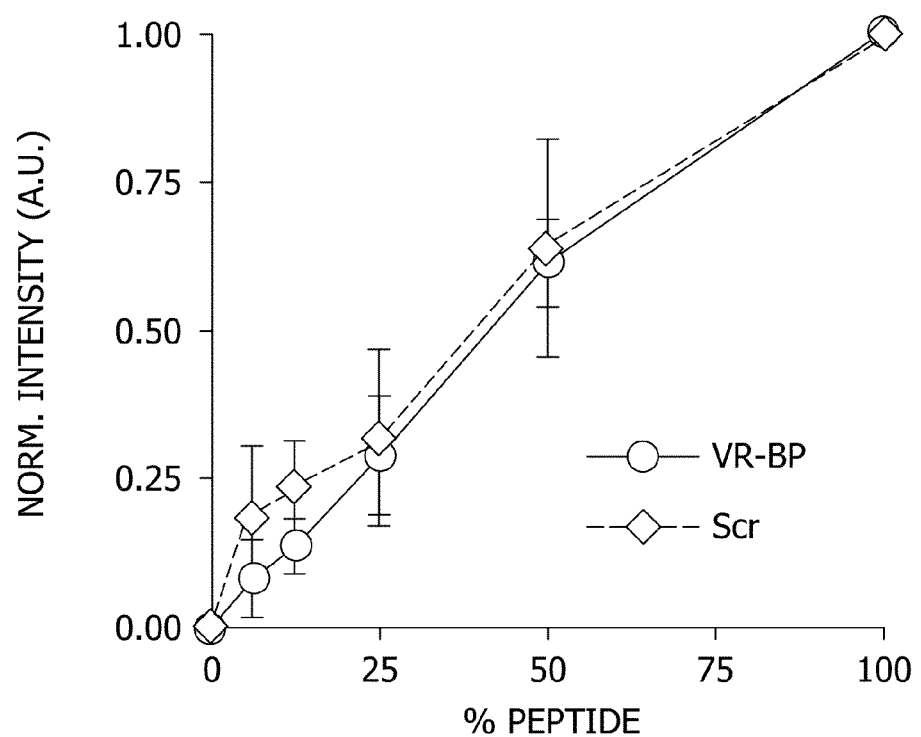
FIG. 24 is a graph illustrating the normalized fluorescent intensity of SAM array spots presenting VR-BP peptide and scrambled peptide (Scr) mixed with ligand as discussed in Example 9 (Error bars indicate standard deviation. % peptide refers to the percent of either VR-BP or scramble present during covalent coupling.).

Ligand immobilization on SAM array spots was visualized using an amine reactive fluorescent molecule to label the lysines present in VR-BP and the scrambled ("Scr") peptide. Alexa Fluor® 488 sulfodichlorophenol ester (Invitrogen, Eugene, Oreg.) was used to label epsilon primary amine groups present in lysine residues of immobilized peptides. Arrays were generated by reacting peptide solutions containing varied percentages of (GRGDSP, SEQ ID NO:18) and VR-BP or scrambled peptide (at a total peptide concentration of 300 µM in PBS pH 7.4) with SAM array spots formed using 5 mole percent HS—$C_{11}$-$EG_6$-COOH and 95 mole percent HS—$C_{11}$-$EG_3$-OH. The reactions took place within an elastomeric stencil, such that each spot could incorporate a distinct peptide identity and density. The fluorescent labeling process was performed after peptide conjugation in which the entire surface of the SAM array was exposed to the amine-reactive fluorescent probe. Fluorescent signal was clearly observed in spots containing VR-BP or scrambled peptide but was not detectable in 0% conditions (containing only GRGDSP (SEQ ID NO:18)) indicating that the fluorescent labeling process was specific to the primary amine residues present in the lysine amino acids of VR-BP and scrambled peptide but not GRGDSP (SEQ ID NO:18) (see, FIG. 23). Normalization and quantification of fluorescent intensity yielded no significant differences in VR-BP substrate incorporation compared to scrambled peptide, and both peptides exhibited 1:1 correlations between relative fluorescence intensity and the percentage of soluble peptide used during covalent immobilization (see, FIG. 24). Taken together, these results suggest that VR-BP and scrambled peptide react at similar efficiencies when combined with GRGDSP (SEQ ID NO:18) during conjugation and that covalently immobilized peptide density relates directly to the percentage of peptide present in solution during conjugation.

Example 10

In this Example, cell attachment and attachment to SAM arrays presenting immobilized VR-BP was determined.

Specifically, SAM spots presenting either 1% VR-BP or 1% scrambled peptide and mixtures of (GRGDSP, SEQ ID NO:18) and mutant ligand (GRGESP, SEQ ID NO:19) were prepared as described above. HUVECs and NIH 3T3 fibroblasts (which have no or minimal VEGF-receptor expression) were seeded at a density of 5,000 cells/cm$^2$ and allowed to attach for 1 hour.

Figure 25:
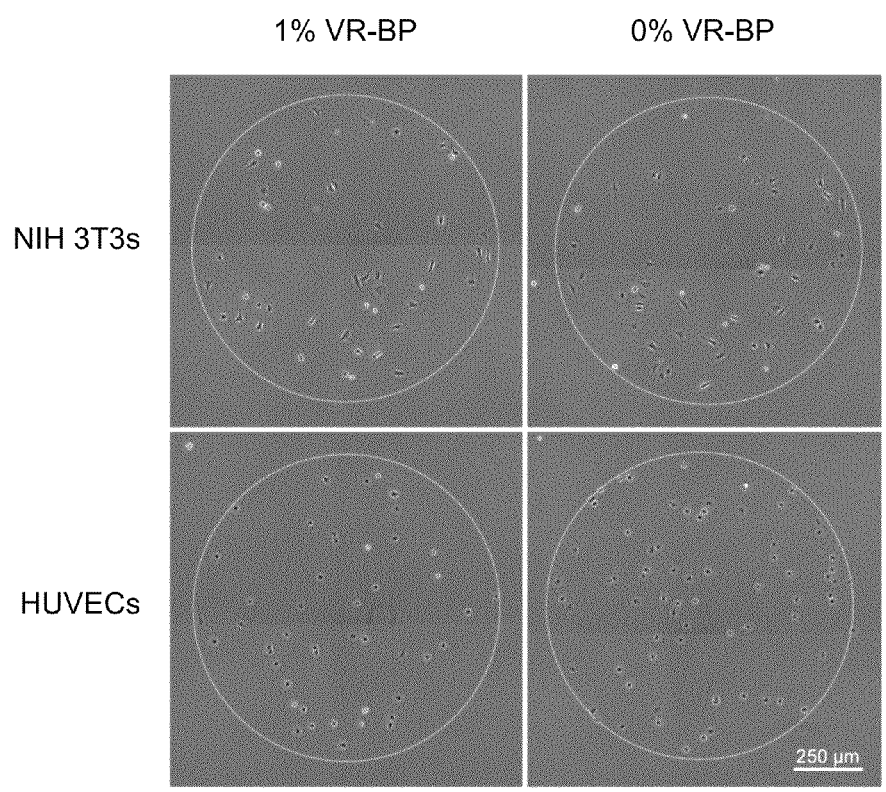
FIG. 25 shows phase contrast images showing attachment of NIH 3T3 cells and HUVECs to SAM array spots presenting varied ligand densities and 1% VR-BP peptide or scrambled peptide (0% VR-BP) as discussed in Example 10.
Figure 26A:
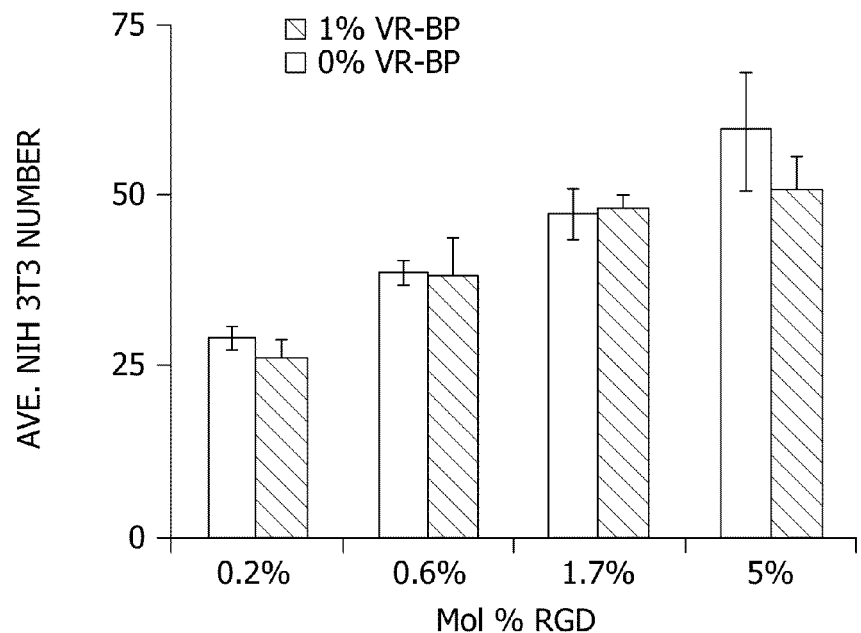
FIGS. 26A and 26B are graphs illustrating the average cell number per spot of (A) NIH 3T3 cells and (B) HUVECs cultured on SAM array spots presenting varied ligand and VR-BP peptide or scrambled (0% VR-BP) as discussed in Example 10.
Figure 26B:
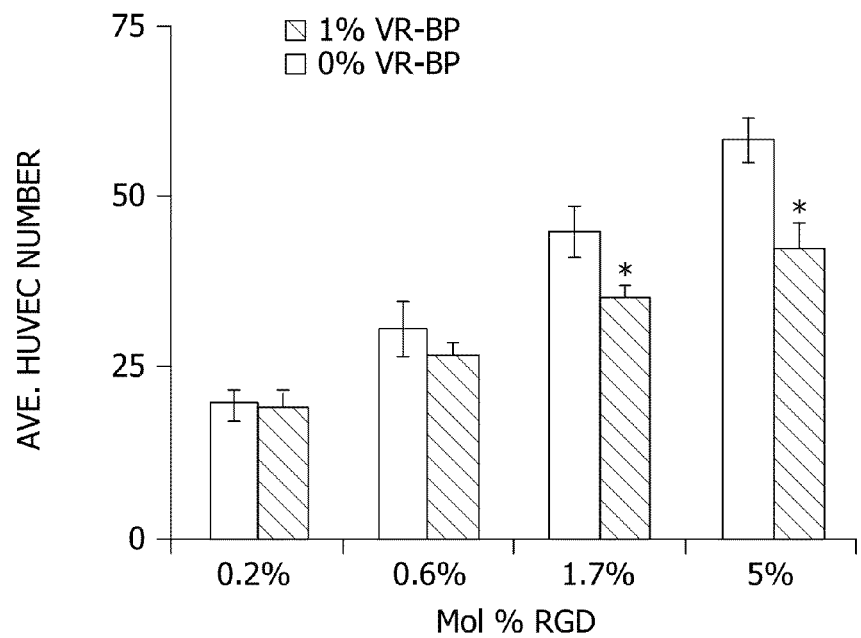
Figure 28A:
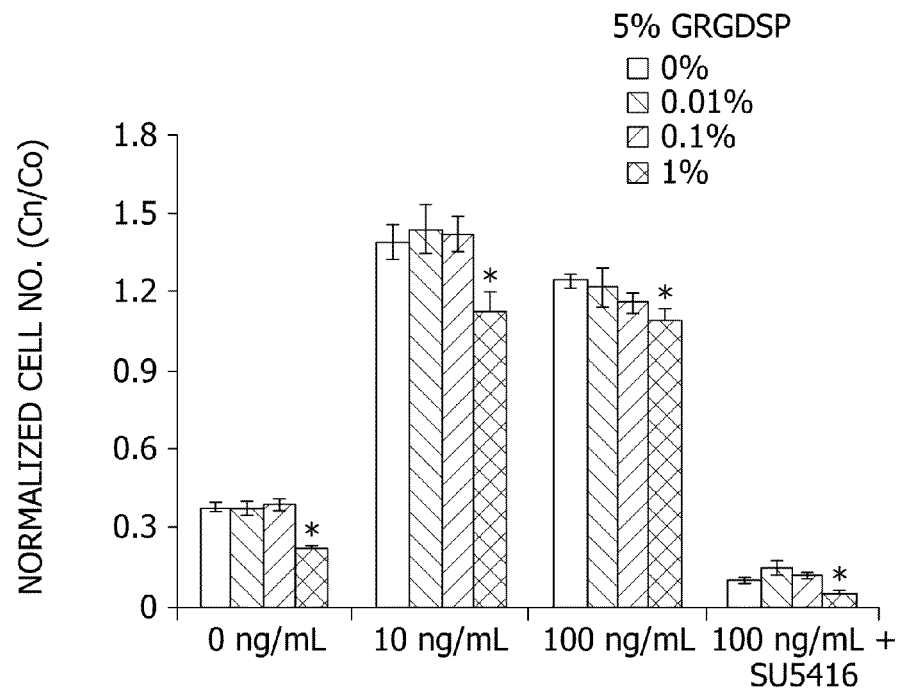
FIGS. 28A and 28B are graphs illustrating proliferation and survival of HUVECs cultured on SAM array spots presenting (A) 5% ligand and (B) 0.5% ligand and 1% VR-BP peptide or scrambled peptide (0% VR-BP) followed by stimulation with VEGF and VEGF+SU5416 as discussed in Example 11.
Figure 28B:
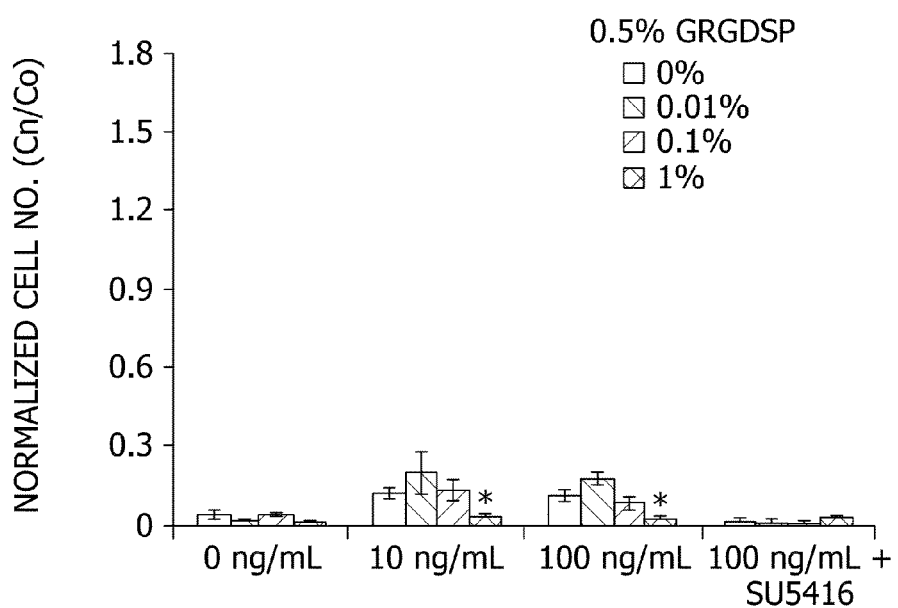

As shown in FIG. 25, both cell types attached to the SAM arrays. Immobilized VR-BP significantly decreased HUVEC attachment to array spots presenting the highest GRGDSP (SEQ ID NO:18) densities (FIG. 28A), while VR-BP had no effect on NIH 3T3 attachment (FIG. 28B). These results suggest that the effects of immobilized VR-BP are specific to cells expressing VEGF receptors (see, FIGS. 26A and 26B).

Example 11

In this Example, the effect of immobilized VR-BP on soluble VEGF signaling was analyzed.

Figure 27A:
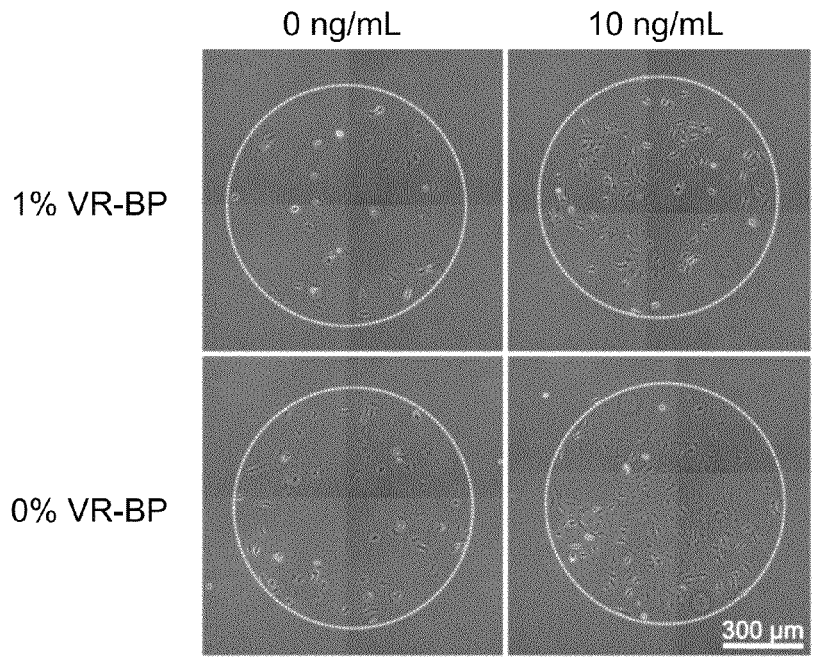
FIGS. 27A and 27B are phase contrast images showing proliferation and survival of HUVECs cultured on SAM array spots presenting (A) 5% ligand and (B) 0.5% ligand and 1% VR-BP peptide or scrambled peptide (0% VR-BP) followed by stimulation with VEGF and VEGF+SU5416 as discussed in Example 11.
Figure 27B:
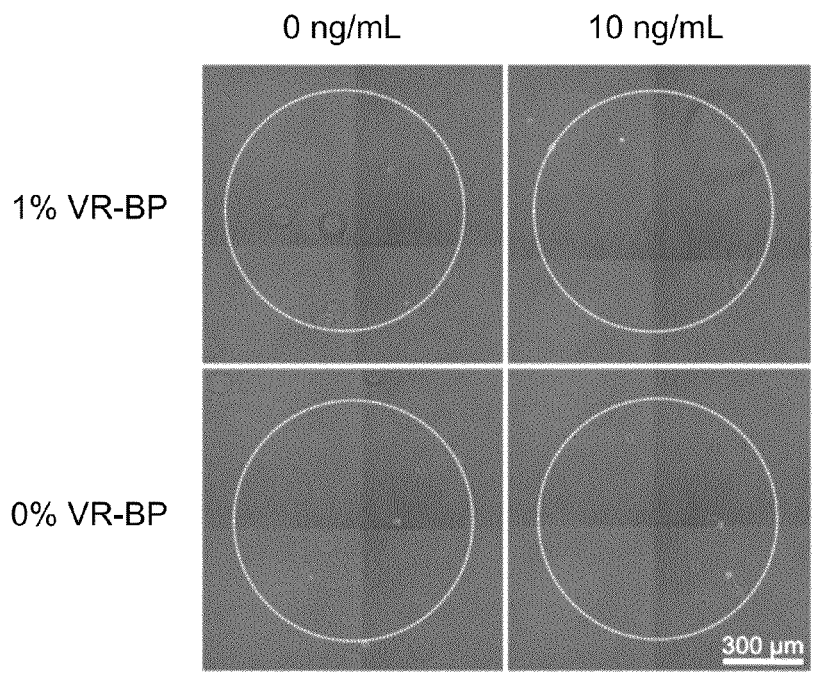

HUVECs were cultured on SAM arrays presenting varied densities of VR-BP (1% VR-BP to 0% VR-BP, where 1-X %=% scrambled peptide) and varied densities of GRGDSP (SEQ ID NO:18) in different soluble environments (FIGS. 27A and 27B). Immobilized VR-BP at 1% density decreased HUVEC survival in conditions without soluble VEGF, or in the presence of a pharmacological inhibitor of VEGF signaling (SU5416) (FIGS. 28A and 28B). Additionally, 1% VR-BP inhibited proliferation in the presence of soluble VEGF at both high and low ligand densities (FIGS. 28A and 28B). Taken together, these results indicate that, unlike the soluble form of VR-BP that exhibits mitogenic effects, substrates presenting covalently immobilized VR-BP not only block HUVEC attachment and proliferation, but also antagonize the effects of soluble VEGF signaling. It is noteworthy that the antagonist effect of immobilized VR-BP was also observed in the presence of the pharmacological inhibitor SU5416, suggesting that covalently immobilized VR-BP can antagonize VEGF signaling in concert with VEGFR tyrosine kinase inhibition.

Example 12

In this Example, endothelial tubulogenesis on SAM spots presenting VR-BP was determined.

Specifically, SAM arrays seeded overnight with 50,000 HUVECs/cm$^2$ were rinsed with warm media and then flipped over onto cold matrigel (Growth factor reduced matrigel, BD Biosciences, Bedford, Mass.) in a rectangular multidish well containing varied concentrations of soluble recombinant VEGF. Matrigel was allowed to gel for 5 minutes, and then the array and matrigel layer were covered with warm m199 with 2% FBS. Arrays were then placed in a TIZ Tokai Hit incubated, humidified stage at 37° C. and 5% CO$_2$ and each array spot was imaged using phase contrast microscopy every 15 minutes for 48 hours. Image analysis was performed using NIS Elements software. The total cell area and length of individual objects were measured in each array spot at 24 hours after seeding. To measure mean length of capillary-like structures, each image was contrasted and thresholded using a standard method to isolate elongated objects for automated length measurements. All objects with a length less than 20 μm were excluded from length measurements. To measure total area occupied by cells, the images were contrasted and thresholded to isolate all cell bodies from the background for automated area measurements. Objects with a length less than 10 μm were excluded from area measurements. Tubulogenesis in each spot was quantified by normalizing the mean length of objects to total cell area in each array spot. SAM array spots were imaged using a Nikon Eclipse Ti inverted microscope with a 10×PhL objective, equipped with Nikon's Perfect Focus System. 10× images were stitched using Nikon NIS Elements software to capture entire array spots and cell counting was performed using the cell counting application in NIS Elements. Statistical analysis of all data sets was performed using a two-tailed student's t-test, where p<0.05 is used to denote statistical significance.

Figure 29:
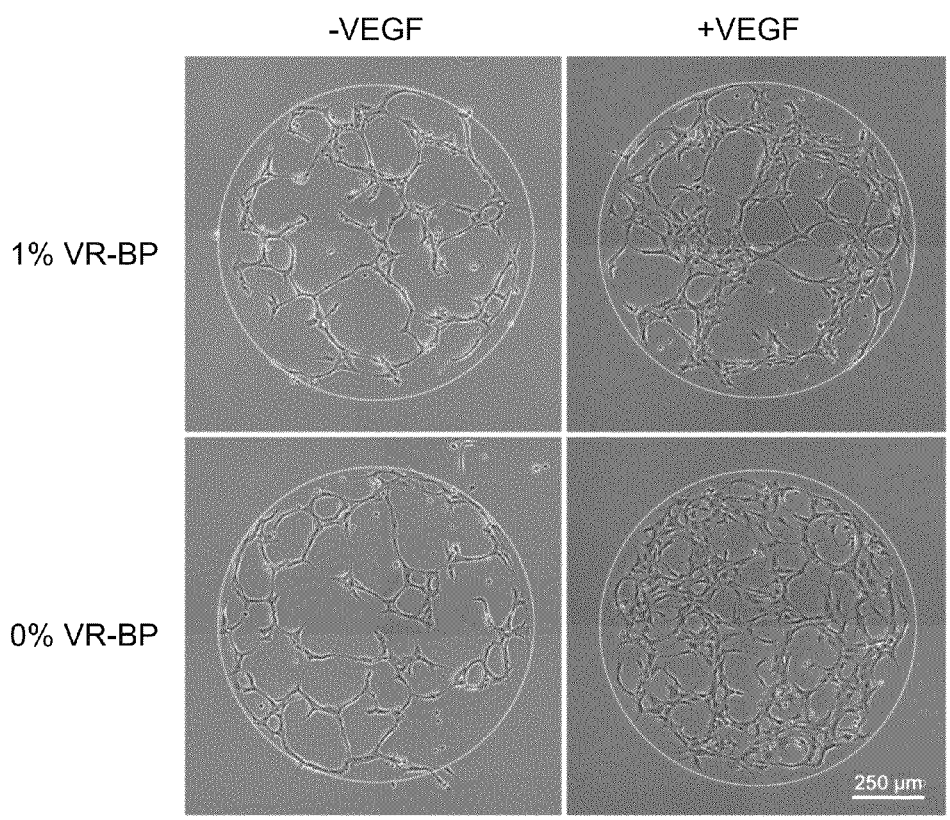
FIG. 29 shows phase contrast images showing endothelial tubulogenesis on SAM array spots presenting 5% ligand and VR-BP (1% VR-BP) or scrambled peptide (0% VR-BP) followed by stimulation with VEGF as discussed in Example 12.
Figure 30:
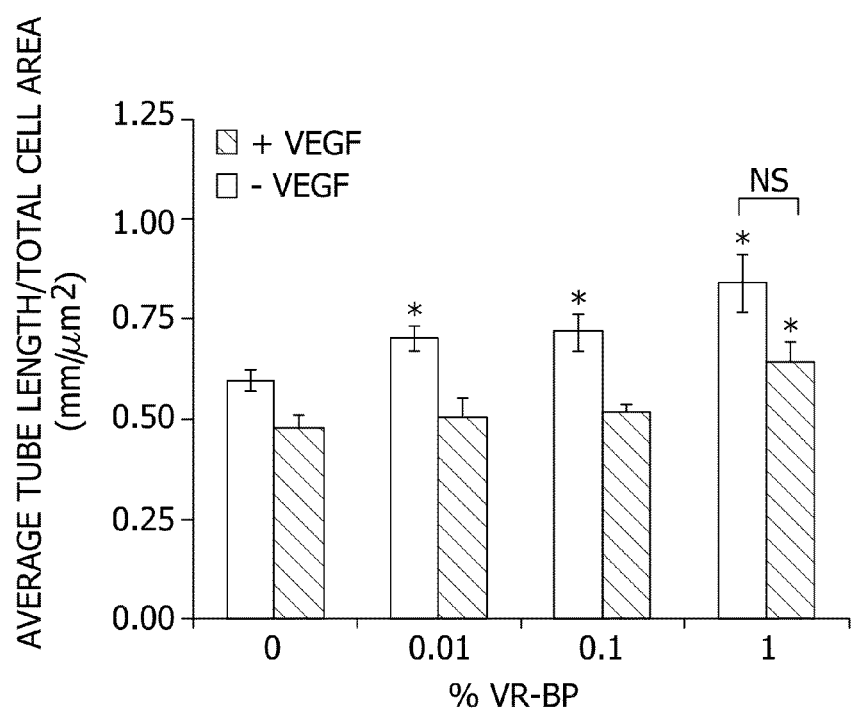
FIG. 30 is a graph illustrating endothelial tubulogenesis on SAM array spots presenting 5% ligand and VR-BP (1% VR-BP) or scrambled peptide (0% VR-BP) followed by stimulation with VEGF as discussed in Example 12 (Error bars represent standard error of the mean. Asterisk indicates significant increase compared to 0% VR-BP and "NS" indicates no significance between soluble VEGF conditions, $p<0.05$).

Tubulogenesis significantly increased on surfaces presenting 1% VR-BP as compared to lower VR-BP surfaces in the absence of soluble VEGF, whereas soluble VEGF protein decreased tubulogenesis by HUVECs (FIG. 29). Thus, immobilized VR-BP inhibited the effects of soluble VEGF protein on tubulogenesis to increase tubulogenesis. When quantified, soluble VEGF decreased tubulogenesis, as quantified by average tubule length per total cell area (FIG. 30). In contrast, 1% VR-BP increased tubulogenesis when compared to 0% VR-BP, both in the presence and absence of soluble VEGF. Therefore, as observed for endothelial cell attachment and proliferation, immobilized VR-BP antagonizes the effects of soluble VEGF on endothelial cell tubulogenesis.

When presented to cells in an insoluble context, covalently immobilized VR-BP inhibited several pro-angiogenic HUVEC behaviors, including attachment and proliferation, and also inhibited HUVEC response to soluble recombinant VEGF protein. Furthermore, substrates with covalently immobilized VR-BP also modulated HUVEC tubulogenesis when a matrigel overlay assay was used to provide cells with a pseudo-three dimensional environment. These results demonstrated that the context in which ligands are presented to cell surface receptors strongly influences their effects, and that the same ligand can be an agonist or an antagonist depending on the manner of presentation to the cell.

The examples described above demonstrate that the methods of preparing the SAM arrays according to the present disclosure offer the ability to rapidly identify substrate components for influencing cell attachment, spreading, proliferation, migration, and differentiation. Additionally, the SAM arrays of the present disclosure support the culture of a range of cell types including hMSCs, HUVECs, NIH 3T3 fibroblasts, human dermal fibroblasts (hDFs), human fibrosarcoma cells (HT-1080s), and human embryonic stem cells (hESCs). Advantageously, the methods used to prepare SAM arrays allow for controlling SAM spot-to-spot conditions such as ligand identity and ligand density, which allows for preparing a wide range of SAM spots in a single array format. This will allow for determining important substrate components for use in cell attachment, spreading, proliferation, migration, and differentiation.

In view of the above, it will be seen that the several advantages of the disclosure are achieved and other advantageous results attained. As various changes could be made in the above devices and methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for preparing a self-assembled monolayer array comprising:
   adhering a polymer stencil to a metal-coated substrate, wherein the polymer stencil comprises at least one well;
   forming at least one alkanethiolate self-assembled monolayer spot on the metal-coated substrate, wherein the alkanethiolate self-assembled monolayer spot is formed in the at least one well of the polymer stencil;
   removing the polymer stencil from the metal-coated substrate; and
   backfilling a region on the metal-coated substrate that surrounds the alkanethiolate self-assembled monolayer spot, wherein the backfilling forms an alkanethiolate self-assembled monolayer surrounding the at least one alkanethiolate self-assembled monolayer spot.

2. The method of claim 1, further comprising immobilizing a ligand on the alkanethiolate self-assembled monolayer spot.

3. The method of claim 2, wherein the ligand is immobilized to an alkanethiol prior to forming the at least one alkanethiolate self-assembled monolayer spot.

4. The method of claim 2, wherein the ligand is immobilized using at least one of carbodiimide chemistry, azide-alkyne cycloaddition chemistry, and maleimide chemistry.

5. The method of claim 2, wherein the ligand is selected from the group consisting of a protein, a nucleic acid, a polysaccharide, a lipid, and combinations thereof.

6. The method of claim 1, further comprising immobilizing a ligand to the alkanethiolate self-assembled monolayer surrounding the alkanethiolate self-assembled monolayer spot.

7. The method of claim 1, wherein the metal comprises gold, titanium, copper, stainless steel, silver, platinum, ruthenium, rhodium, palladium, osmium, iridium and combinations thereof.

* * * * *